(12) United States Patent
Mujeeb-U-Rahman et al.

(10) Patent No.: US 9,006,014 B2
(45) Date of Patent: Apr. 14, 2015

(54) FABRICATION OF THREE-DIMENSIONAL HIGH SURFACE AREA ELECTRODES

(71) Applicant: California Institute of Technology, Pasadena, CA (US)

(72) Inventors: Muhammad Mujeeb-U-Rahman, Pasadena, CA (US); Axel Scherer, Barnard, VT (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/106,701

(22) Filed: Dec. 13, 2013

(65) Prior Publication Data

US 2014/0167257 A1     Jun. 19, 2014

Related U.S. Application Data

(60) Provisional application No. 61/736,944, filed on Dec. 13, 2012.

(51) Int. Cl.

| | | |
|---|---|---|
| H01L 21/283 | (2006.01) | |
| H01L 21/285 | (2006.01) | |
| H01L 29/41 | (2006.01) | |
| H01L 33/38 | (2010.01) | |
| H01L 31/00 | (2006.01) | |

(52) U.S. Cl.
CPC .......... *H01L 21/28556* (2013.01); *H01L 29/41* (2013.01); *H01L 33/387* (2013.01); *H01L 31/00* (2013.01)

(58) Field of Classification Search
CPC .................................................... H01L 33/387

USPC .......................... 438/49, 668, 702, FOR. 363
See application file for complete search history.

(56) References Cited

U.S. PATENT DOCUMENTS

| | | | |
|---|---|---|---|
| 5,999,849 A | 12/1999 | Gord et al. | |
| 6,259,937 B1 | 7/2001 | Schulman et al. | |
| 6,864,802 B2 | 3/2005 | Smith et al. | |
| 7,348,243 B2 | 3/2008 | Kim | |
| 7,741,664 B2 * | 6/2010 | Choi et al. | 257/291 |
| 7,800,078 B2 | 9/2010 | Colvin, Jr. et al. | |

(Continued)

FOREIGN PATENT DOCUMENTS

| | | |
|---|---|---|
| EP | 2433563 | 3/2012 |
| KR | 10-2005-0066741 | 6/2005 |

(Continued)

OTHER PUBLICATIONS

Seese, T.M., et al., "Characterization of tissue morphology, angiogenesis, and temperature in the adaptive response of muscle tissue in chronic heating", Laboratory Investigation, 1998; 78 (12): pp. 1553-1562.

(Continued)

*Primary Examiner* — George Fourson, III
(74) *Attorney, Agent, or Firm* — Steinfl & Bruno LLP

(57) ABSTRACT

A method for fabricating three dimensional high surface electrodes is described. The methods including the steps: designing the pillars; selecting a material for the formation of the pillars; patterning the material; transferring the pattern to form the pillars; insulating the pillars and providing a metal layer for increased conductivity. Alternative methods for fabrication of the electrodes and fabrication of the electrodes using CMOS are also described.

15 Claims, 44 Drawing Sheets

(56) References Cited

U.S. PATENT DOCUMENTS

| | | | |
|---|---|---|---|
| 8,527,025 | B1 | 9/2013 | Shults et al. |
| 2006/0247539 | A1 | 11/2006 | Schugt et al. |
| 2006/0261406 | A1 | 11/2006 | Chen |
| 2010/0114225 | A1 | 5/2010 | Imran et al. |
| 2010/0215543 | A1* | 8/2010 | Henry et al. .................. 422/68.1 |
| 2014/0001110 | A1* | 1/2014 | Lee et al. .................... 210/323.2 |
| 2014/0011013 | A1* | 1/2014 | Jin et al. ...................... 428/297.4 |
| 2014/0057416 | A1* | 2/2014 | Warren et al. ................. 438/478 |
| 2014/0290057 | A1* | 10/2014 | Lin et al. ......................... 29/846 |

FOREIGN PATENT DOCUMENTS

| | | |
|---|---|---|
| KR | 10-2007-0073430 | 7/2007 |
| KR | 10-2009-0067533 | 6/2009 |
| KR | 10-2009-0098285 | 9/2009 |
| WO | 00-59370 | 10/2000 |
| WO | 2010-075479 | 10/2010 |

OTHER PUBLICATIONS

Ward, K. W., "A Review of the Foreign-body Response to Subcutaneously-implanted Devices: The Role of Macrophages and Cytokines in Biofouling and Fibrosis", *Journal of Diabetes Science and Technology*, vol. 2 (5), Sep. 2008, pp. 768-777.

Ward, K.W., et al., "The effect of microgeometry, implant thickness and polyurethane chemistry on the foreign body response to subcutaneous implants", *Biomaterials*, vol. 23, 2002, pp. 4185-4192.

Henry, M.D., et al., "Alumina Etch masks for Fabrication of High-Aspect-Ratio Silicon Micropillars and Nanopillars", Nanotechnology, 2009, 20 (25), 255305, 4 pages.

Ming Li, Chang; Dong, Hua; Cao, Xiaodong; T. Luong, John H.; Zhang, Xueji, "Implantable Electrochemical Sensors for Biomedical and Clinical Applications: Progress, Problems, and Future Possibilities," Current Medicinal Chemistry, 2007, vol. 14, Issue 8, pp. 937-951 (15).

Guigen Zhang, Chapter 13 "Design and Fabrication of 3D Skyscraper Nanostructures and Their Application as Electrodes" in *Biosensors, New Perspectives in Biosensors Technology and Applications*, Prof. Pier Andrea Serra (2011 Ed.), ISBN: 978-953-307-448-1, InTech Publishers.

Brian S. Ferguson et al., "Integrated Microfluidic Electrochemical DNA Sensor," Anal. Chem. 2009, 81, pp. 6503-6508.

Fang Wei, Peter B. Lillehoj, and Chih-Ming Ho,"DNA Diagnostics: Nanotechnology-Enhanced Electrochemical Detection of Nucleic Acids," Pediatric Research, May 2010; 67(5): pp. 458-468.

Syed M. Usman Ali et al., "Wireless Remote Monitoring of Glucose Using a Functionalized ZnO Nanowire Arrays Based Sensor," Sensors 2011, 11, pp. 8485-8496.

PCT International Search Report mailed on Apr. 30, 2014 issued for PCT/US2013/075192 filed on Dec. 13, 2013 in the name of California Institute of Technology.

PCT Written Opinion mailed on Apr. 30, 2014 issued for PCT/US2013/075192 filed on Dec. 13, 2013 in the name of California Institute of Technology.

PCT International Search Report mailed on May 26, 2014 issued for PCT/US2013/015177 filed on Dec. 13, 2013 in the name of California Institute of Technology.

PCT Written Opinion mailed on May 26, 2014 issued for PCT/US2013/015177 filed on Dec. 13, 2013 in the name of California Institute of Technology.

M.M. Ahmadi et al., "A Wireless-Implantable Microsystem for Continuous Blood Glucose Monitoring", Transaction on Biomedical Circuits and Systems, vol. 3, No. 3, pp. 169-180, 2009.

G. Freckmann et al., "Performance Evaluation of Three Continuous Glucose Monitoring Systems: Comparison of Six Sensors Per Subject in Parallel", Journal of Diabetes Science and Technology, vol. 7, No. 4, pp. 842-853, 2013.

Y.T. Liao et al., "A 3 uW CMOS Glucose Sensor for Wireless Contact-Lens Tear Glucose Monitoring", Journal of Solid-State Circuits, vol. 47, No. 1, pp. 335-344, 2012.

S. O'Driscoll et al., "A mm-sized implantable power receiver with adaptive link compensation", International Solid-State Circuits Conference, pp. 294-295, 2009.

PCT International Search Report mailed on Nov. 11, 2014 issued for PCT/US2014/048087 filed on Jul. 24, 2014 in the name of California Institute of Technology.

PCT Written Opinion mailed on Nov. 11, 2014 issued for PCT/US2014/048087 filed on Jul. 24, 2014 in the name of California Institute of Technology.

* cited by examiner

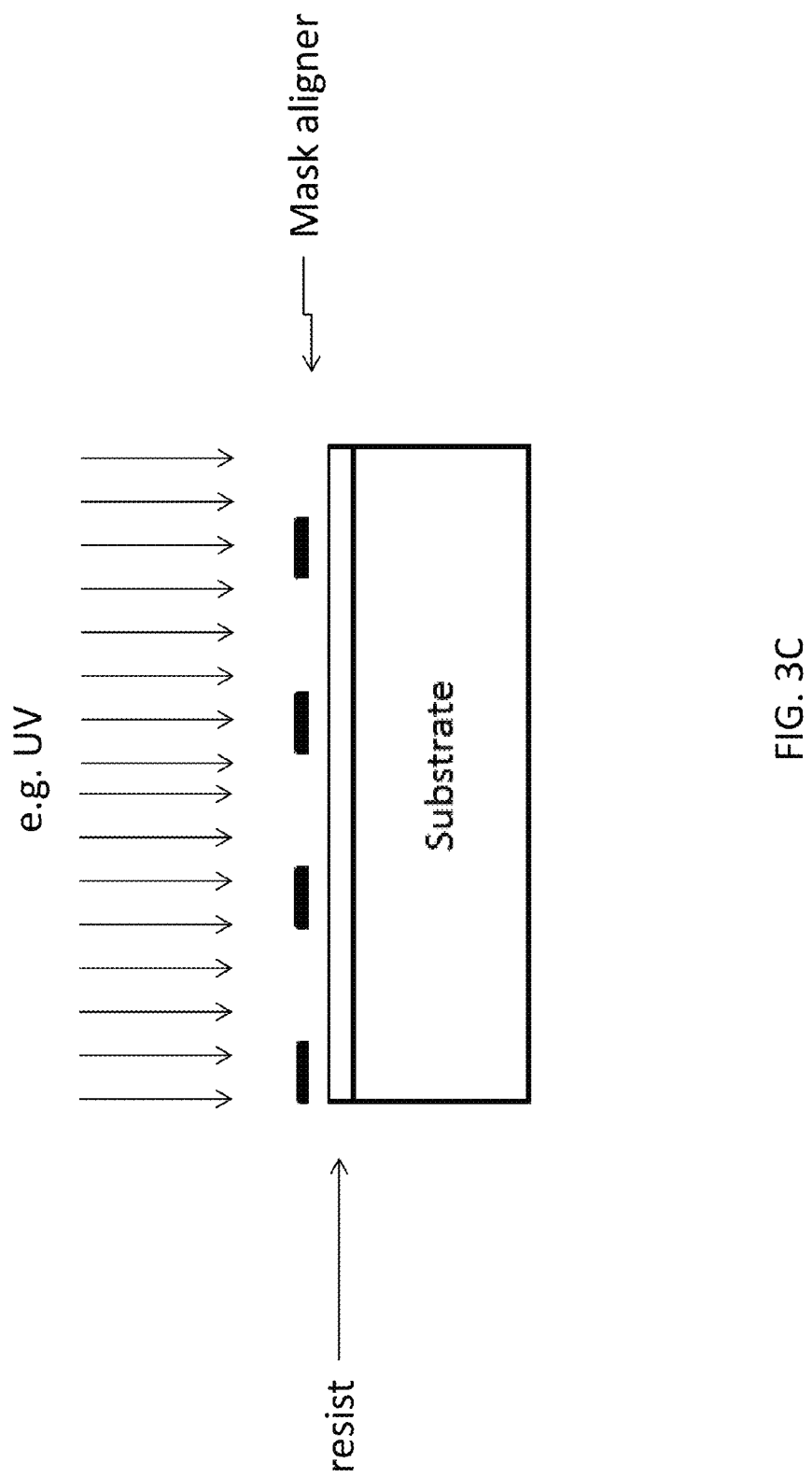

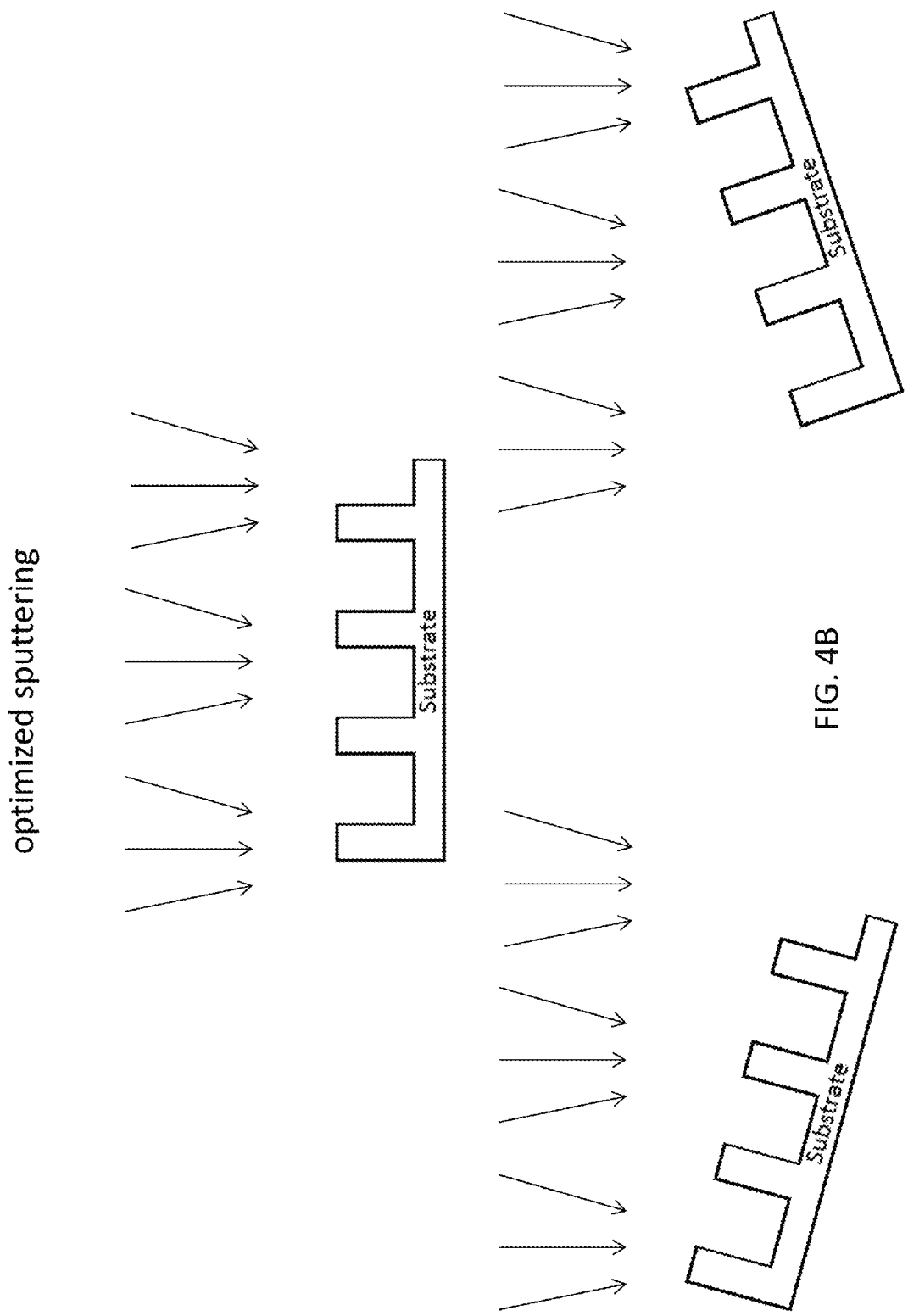

FABRICATION OF THREE-DIMENSIONAL HIGH SURFACE AREA ELECTRODES

CROSS REFERENCE TO RELATED APPLICATIONS

The present application claims priority to U.S. Provisional application 61/736,944 filed on Dec. 13, 2012, which is incorporated herein by reference in its entirety.

TECHNICAL FIELD

The present disclosure relates to electrodes. More particularly, it relates to a fabrication of three-dimensional high surface area electrodes.

BACKGROUND

One of the many aspects to consider when fabricating an implantable sensor is minimizing the foreign body reaction to the implantable sensor. In particular, an aim would be minimizing the complexity of the process for implanting the sensor and the resultant damage which may occur during the implantation.

High surface area electrodes with very small geometrical areas can help achieve the above goal while retaining sensitivity for sensing applications. Additionally, the use of the high surface area electrodes can also decrease the system cost, for example, when used with existing CMOS (complementary metal-oxide-semiconductor) technology.

Micro-scale and nano-scale structuring of electrodes have been used in sensing and energy storage. Such structuring of electrodes can also provide advantages in terms of high output signal and enhanced selectivity using different sensing techniques.

The most common fabrication methods for making such high surface area electrodes include direct Physical Vapor Deposition (PVD) or Chemical Vapor Deposition (CVD) for the electrode materials. However, the resulting structures for the electrodes fabricated using either PVD or CVD are not suitable for long-term use. For example, such electrodes can experience deformation in when subjected to liquid environments because of existing capillary forces in the environments.

Alternative bottom-up fabrication techniques which could be used to make high surface area electrodes include vapor-liquid-solid (VLS) growth, porous templates or complex electrochemical plating. Although the devices fabricated using bottom-up fabrication techniques function better in liquids than the electrodes fabricated using PVD or CVD, there are a number of different complications which arise. First, VLS uses high temperatures, high pressures and phase transitions which cannot be easily controlled. Additionally, porous templates require fabrication of porous templates and filing templates. Furthermore, electrochemical plating requires the use of liquids. In view of such requirements, these bottom-up fabrication techniques may not be compatible with current CMOS processes or other standard fabrication processes used in making implantable systems. Therefore, these bottom-up fabrication techniques can be pretty complex, expensive and difficult to replicate.

SUMMARY

According to a first aspect of the present disclosure, a method for fabricating three dimensional high surface electrodes is provided, the method comprising designing a plurality of pillars by optimizing one or more characteristics of the pillars, wherein the plurality of pillars corresponds to one or more electrodes dependent on an isolation provided to the plurality of pillars; applying a resist onto a substrate, wherein the substrate is silicon or silicon alloy; patterning the resist, wherein the patterning defines the plurality of pillars to be formed on the substrate; removing selected portions of the substrate via etching corresponding to the pattern of the resist to form the plurality of pillars, the etching forming a pillar with an aspect ratio greater than 5; insulating a first group of pillars of the plurality of pillars from other pillars of the plurality of pillars to form one distinct electrode by forming an insulator layer with complete and uniform coverage over the first group of pillars of the plurality of pillars; and depositing a 10 nm to 500 nm metal layer on the plurality of pillars to increase the conductivity of a surface of the electrode, wherein the metal layer coverage is complete and uniform over the plurality of pillars.

According to a second aspect of the present disclosure, a method for fabricating three dimensional high surface electrodes from CMOS on a metal that is not silicon is presented, the method comprising: designing a plurality of pillars by optimizing one or more characteristics of the pillars, wherein the plurality of pillars corresponds to one or more electrodes dependent on the isolation provided to the plurality of pillars; selecting a top most metal layer from the CMOS where the pillars will be formed, wherein the top most metal layer is not silicon; applying a resist onto the top most metal layer of the CMOS; patterning the resist, wherein the patterning defines where the plurality of pillars will be formed on the top most metal layer of the CMOS; removing selected portions of the top most metal layer of the CMOS via etching corresponding to the pattern of the resist to form the plurality of pillars, the etching forming a pillar with an aspect ratio greater than 5; and depositing a 10 nm to 500 nm metal layer on the plurality of pillars to increase conductivity of a surface of the electrode, wherein a coverage of the metal layer coverage is complete and uniform over the plurality of pillars, wherein the method for fabricating is performed at temperatures<500° C.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIGS. 3A-3H illustrate the steps of the fabrication method starting from a substrate, using etching and deposition of insulation and metal layers.

FIGS. 4A and 4B illustrate exemplary embodiments of metal deposition.

DETAILED DESCRIPTION

Methods for designing and fabricating high surface area electrodes are described with embodiments in this present disclosure. In particular, the present disclosure describes methods of designing and fabricating pillars which are then used as an electrode for sensing applications. It should be noted that a plurality of pillars, etched or grown from a substrate (e.g. silicon), correspond to one or more electrodes based on the insulation provided to electrically isolate a group of pillars from other pillars (discussed later).

As referenced in this present disclosure, the term "nanopillar" or "micropillar" refers to pillars being formed using the method of the present disclosure in terms of nano-scale or micro-scale, respectively.

Figure 1:
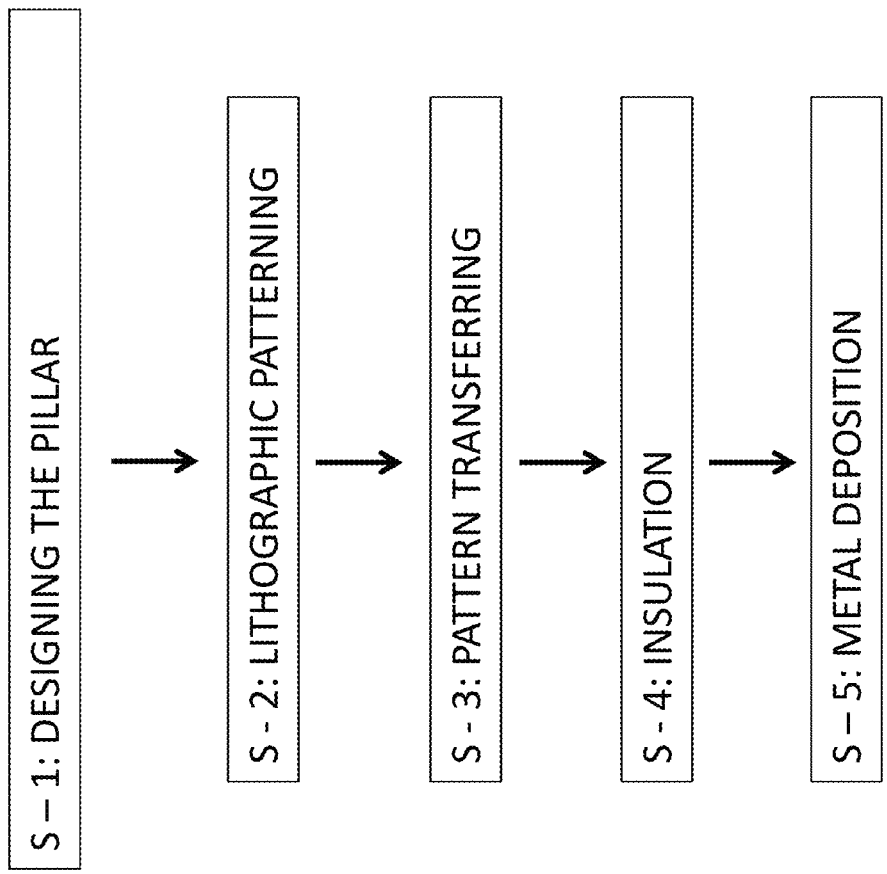
FIG. 1 illustrates a flowchart depicting steps performed in the fabrication method of the present disclosure.

With reference to FIG. 1, a flow chart is provided to illustrate the steps associated with an embodiment of the present disclosure for designing and fabricating the high surface area electrodes. The method has the following steps:

1) designing the pillars to be fabricated based on a selected application,
2) lithographic patterning of a substrate where the pillars will be formed,
3) pattern transferring to form the pillars,
4) insulation of the pillars to define the electrodes, and
5) metal deposition for increased conductivity for the electrodes.

Further details concerning the above steps are provided below. It should be noted that the methods for the above steps are performed at room temperature. The use of room temperature is important because it allows the method to be applicable for use with a variety of materials when forming the pillars without concern for potentially damaging other structures or elements which may be found near the fabrication site (e.g. in the substrate) arising from use of extreme temperatures.

Additionally, the present disclosure also describes alternative embodiments for the discussed methods of fabrications of the electrode. In particular, details will be provided for adapting the method described above for use with CMOS technology as opposed to a substrate (e.g. silicon). Furthermore, an alternative hybrid fabrication method for fabricating the pillars for increased surface area will also be described.

Designing the Pillars

Based on a desired application for the electrode, parameters of the pillars (corresponding to one or more electrodes) are optimized. For some embodiments of the present disclosure, a parameters to be optimized is sizing of the pillars. For example, an electrode can be sized based on the intended target to be detected. If cells are to be detected using the pillars, an embodiment may design the pillars using micro-scale. The exact size will depend on the size of the particular cells. However, if proteins are to be detected (which are of a smaller scale) by the pillars, the embodiment according to the present disclosure may design the pillars using nano-scale. Another design aspect is the top material of the pillars which will depend on the application. Further discussion about this aspect will be provided below in the discussion for metal deposition.

The detailed design of the electrodes with pillars is generally performed using commercially-available software adapted to perform simulations and modeling of the pillars.

Figure 2:
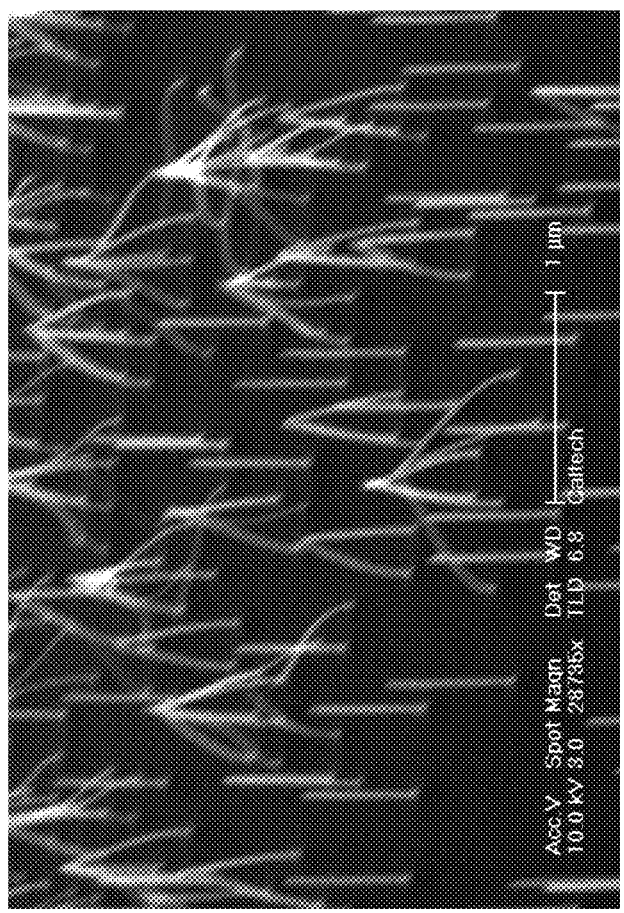
FIG. 2 illustrates exemplary embodiments where plasma-etched pillars with high aspect ratio (~25) demonstrating bending because of liquid surface tension forces.

In embodiments according to the present disclosure, design of other parameters for the pillars are as follows:
- diameters for the pillars are between 50 nm to 1 micron (e.g. between 100 nm and 500 nm),
- heights for the pillars are between 100 nm to 20 microns (e.g. between 250 nm and 1 micron), and
- aspect ratio (which is a relationship between the height and width) for the pillars. In particular for embodiments where the pillars are designed for use in liquids, the aspect ratios for the pillars are around 20. For other embodiments where the pillars are designed for use in air, the aspect ratios for the pillars are around 30. It should be noted that with higher aspect ratios, bending may occur with the pillars (see, FIG. 2).

Lithographic Patterning

Figure 3A:
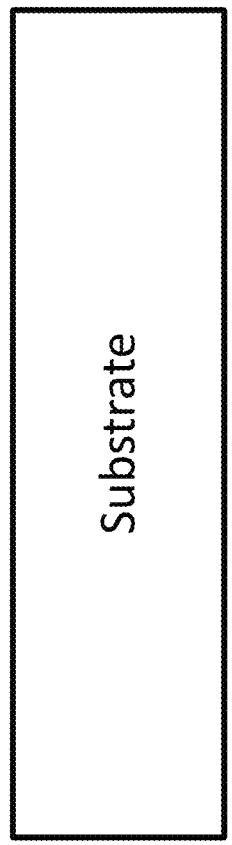

After the design of the pillars is confirmed, fabrication of the pillars begins. First, in the lithographic patterning step, a substrate (e.g. a silicon wafer) is selected (see, FIG. 3A). The type of substrate chosen may depend on the application of the electrode. For example, embodiments according to the present disclosure may choose to use silicon as a substrate for the formation of electrodes associated with non-implants, microfluidics, lab-on-a-chip, etc. . . . . In these cases, electronics can be later associated with the electrode for use in the sensor system.

Alternative, embodiments according to the present disclosure may choose a CMOS die as the substrate. Examples of commercially available CMOS dies include TSMC 250 nm and IBM 250 nm. A benefit for using a commercially available CMOS die may include the ability to use already existing circuitry CMOS for control therefore removing a need to provide separate circuitry to control the system. Furthermore, insulation is already provided. Lastly, fabrication of such dies are already available therefore reducing costs compared to situations where substrates may need to be designed for use for a sensor. Embodiments where the CMOS is used will be discussed later in this present disclosure.

Figure 3B:
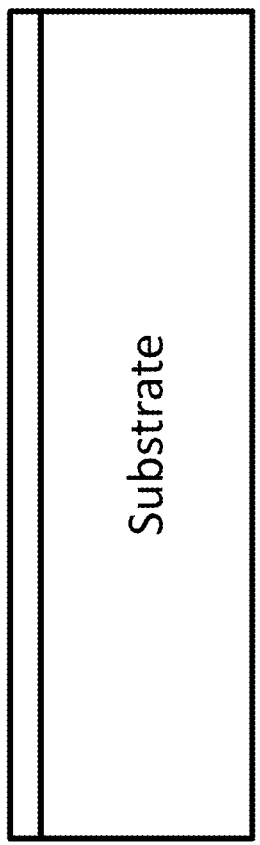

Next in the lithographic patterning step, the method defines where the pillars will be formed on the chosen substrate through the use of a resist (e.g. a photoresist or electron resist) (see, FIG. 3B). The type of resist used can depend on the parameters of the pillars (e.g. micro-scale or nano-scale) to be formed as well as the type of lithography (e.g. photo lithography or e-beam lithography) used. Examples of photo resists which may be used in various embodiments according to the present disclosure include: AZ5214E, S1813, S1818 and SU8. The chosen photo resist can be spun or sprayed onto the substrate using spin-coating or spray-coating techniques as known in the present state of the art.

After the photo resist has been applied onto the substrate, patterning of the photo resist occurs. In an embodiment of the present disclosure, photo lithography (or optical lithography) is performed by using a mask aligner (e.g. Carl Suss MA6 or MJB3) (see, FIG. 3C). The mask aligner dictates where the pillars will form on the substrate by covering the areas of the substrate corresponding to where the pillars will be formed. Generally all other areas not covered will be removed (e.g. through etching). The photo resist is then baked at high temperatures (e.g. ~1000° C.) or exposed to ultra-violet (UV) or deep-UV at various intensities.

Figure 3D:
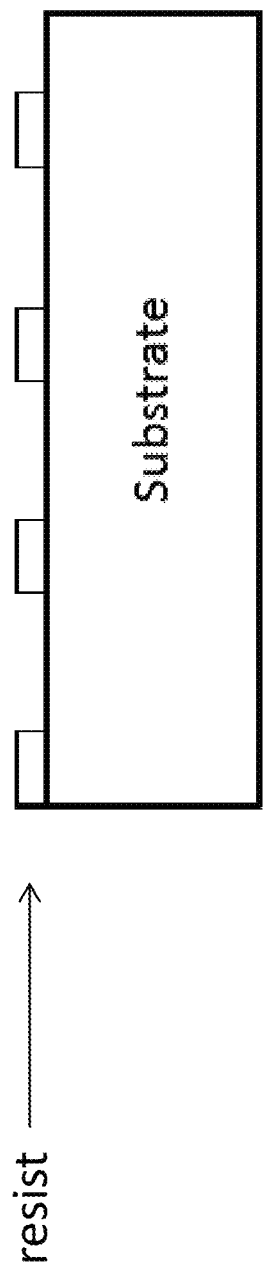

After the baking or exposure above has occurred, development is performed whereby selective portions of the photo resist (in particular the parts of the photo resist which was left exposed through the mask aligner) on the substrate are removed. The resulting product is an exposed substrate with portions of the substrate still covered in a layer of photo resist (see, FIG. 3D). These areas of the substrate which are still covered in photo resist correspond to where the pillars will be formed while the areas of the substrate without photo resist will be removed (e.g. etching). In embodiments of the present disclosure, the selective portions of the resist are removed using a solution (e.g. MF319, AZ300, CD26).

Aside from optical lithography, e-beam lithography can be used where electron resists can be utilized (e.g. PMMA950A4, MA-N, and FOX). Electron resists can also be spun or sprayed onto the surface of the substrate using the spin-coating or spray-coating techniques described above with reference to photo resists. For e-beam lithography, an electron beam pattern generator is used (e.g. Vistec 5000+, Jeol, FEI) to produce the pattern directly onto the electron resist. In this way a mask aligner is not used. The electron resist is then baked or exposed. Furthermore, MA-D or a mixture of MIBK and IPA is used during development when removing the selective parts of the electron resist covering the areas of the substrate to be removed (e.g etching).

It should be noted that the type of lithography used can depend on the scaling for the pillars. For example, an embodiment of the present disclosure may use e-beam lithography if the design of the pillars is of a nano-scale design. Meanwhile, photolithography would be applicable for micro-scale designs. There are situations where photolithography could be applicable for nano-scale design of pillars. However, these situations may be expensive and time consuming to implement.

Step 2—Pattern Transfer

Figure 3E:
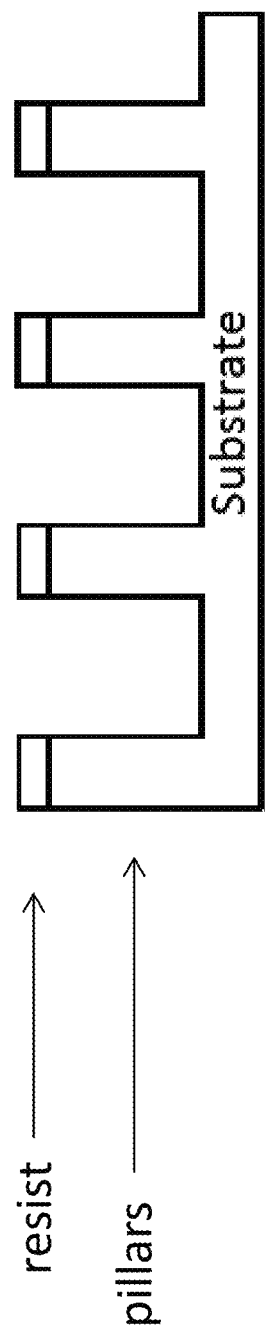

After the resist has been removed from the selective sections of the substrate, the next step for the fabrication of the electrode is to transfer the pattern from the resist into the substrate. In particular, embodiments of the present disclosure associate this step of pattern transfer with top-down etching (see, FIG. 3E). Alternatively, pattern transfer can also be performed via a hybrid of top-down bottom up fabrication methods (which will be described in further detail below).

According to embodiments of the present disclosure, the term "top-down etching" refers to the formation of pillars from a substrate caused by the removal of substrate (via the process of etching) surrounding the sections of the substrate which will become the pillars. The removal of the surrounding substrate is performed using an etching material. This generalization of "top-down" formation of pillars is in contrast to the formation of pillars using a "bottom-up" technique. In this "bottom-up" method, pillars are grown from a catalyst on a given substrate. Embodiments of the present disclosure choose to use the top-down method of forming pillars because such methods can be readily replicated in commercially available foundries. With respect to "bottom-up" fabrication, such methods may be expensive, time consuming and are not compatible with existing methods in existing foundries.

As stated above, the methods of fabrication are chosen to be performed at room temperature. In particular, it should be noted that the etching in embodiments of the present disclosure is performed at room temperatures in order to avoid providing stress and/or damage to underlying structures in the substrate (especially if the material being etched on is CMOS).

With respect to the "top-down" etching of the present disclosure, such room-temperature etching is performed using a silicon plasma etch. An example of the silicon plasma etch which is used is described in Henry ("Alumina Etch masks for Fabrication of High-Aspect-Ratio Silicon Micropillars and Nanopillars") where such etch has been developed and optimized for use in the methods described in the present disclosure. The silicon plasma etch is optimized to achieve embodiments which have uniform etch depth for all pillar widths and uniform sidewall roughness.

Insulation

Figure 3F:
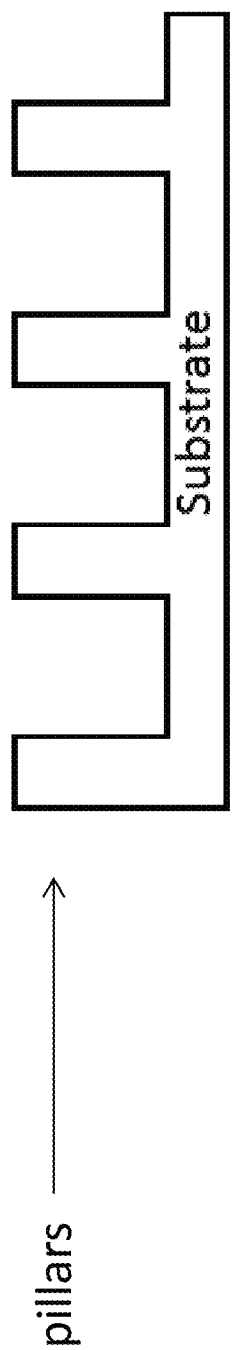
Figure 3G:
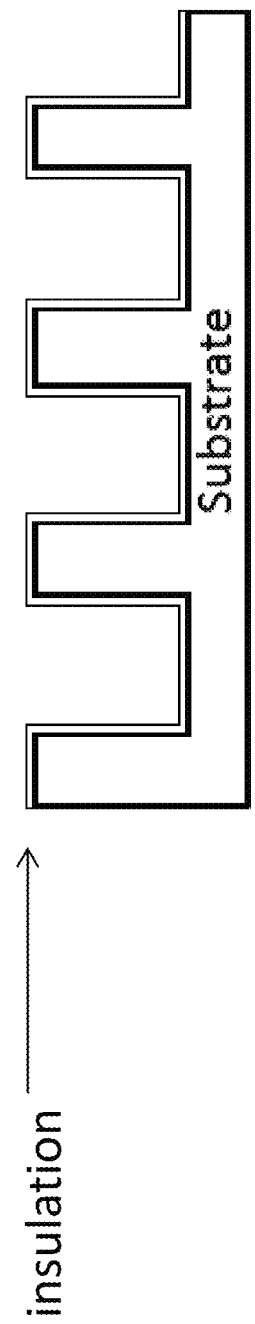

Following the formation of the pillars (see, FIG. 3F), an insulation step is performed (see, FIG. 3G). This step isolates groups of pillars from other groups of pillars on a substrate thereby forming separate electrodes which are not electrically connected to each other. If these pillars are not properly isolated from other pillars (corresponding to the situation where the pillars are all electrically connected to each other), the pillars would then act as one electrode.

Insulation can be performed in a number of ways. In an embodiment of the present disclosure, thermal oxidation can be performed. In this method, oxides or nitrides are formed on the surface of the pillars through the use of extremely high temperatures (~1000° C.). Although the method of creating the oxides or nitrides may be easy, if the substrate, where the pillars are being formed on, is sensitive to extreme temperatures (e.g. as in the case with using CMOS), then damage to the underlying structures of the substrate can occur.

Alternatively, embodiments using lower temperatures (or even room temperature) are possible. For example, plasma oxidation can be performed where the substrate is placed in a machine with oxygen plasma at ~200° C. in order to grow an oxide layer to be used for insulation.

However, for a number of embodiments of the present disclosure, insulation is performed by depositing insulating material (oxides or nitrides) onto the pillars directly. The insulating materials are deposited onto the pillars in a manner similar to the metal deposition discussed below. The use of this insulating technique allows the embodiment to avoid high temperatures that may be present in thermal oxidation which can damage other elements in the overall system. However, as discussed below, the method of depositing the insulating materials in a similar manner as the metal deposition may be more complicated than the above two methods (e.g. thermal oxidation or plasma oxidation) described.

Metal Deposition

Figure 3H:
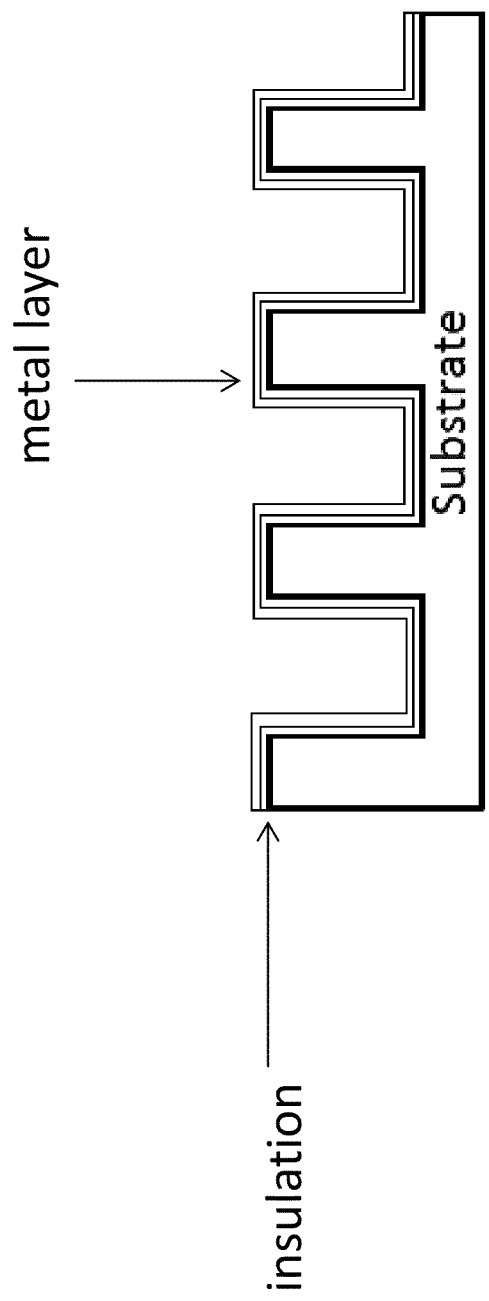

Lastly, the method of fabrication concludes with the deposition of a metal layer on the formed pillars (see, FIG. 3H). The metal layer increases the conductivity of the plurality thereby increasing the conductivity of the electrode surface. It also makes the surface of the pillars more sensitive to some species for detection purposes. A variety of different metals can be used depending on the application of the electrode. Depending on the target object being detected/measured, particular metals may be more effective in detecting the object because of the increased sensitivity. For example, some embodiments of the present disclosure use platinum when detecting glucose while other embodiments of the present disclosure use gold if DNA is going to be detected.

Additionally, a variety of methods for metal deposition onto the pillars can be also used. It should be noted that to ensure the electrode operates as anticipated, a uniform and complete coverage of the pillars in the metal layer is provided.

Typically a metal layer can be provided onto the pillars using methods such as electron beam evaporation or ion beam induced deposition. However, it was found that the pillars were not completely and continuously covered. In particular, coverage of the sides of the pillars was not complete and uniform.

Figure 4A:
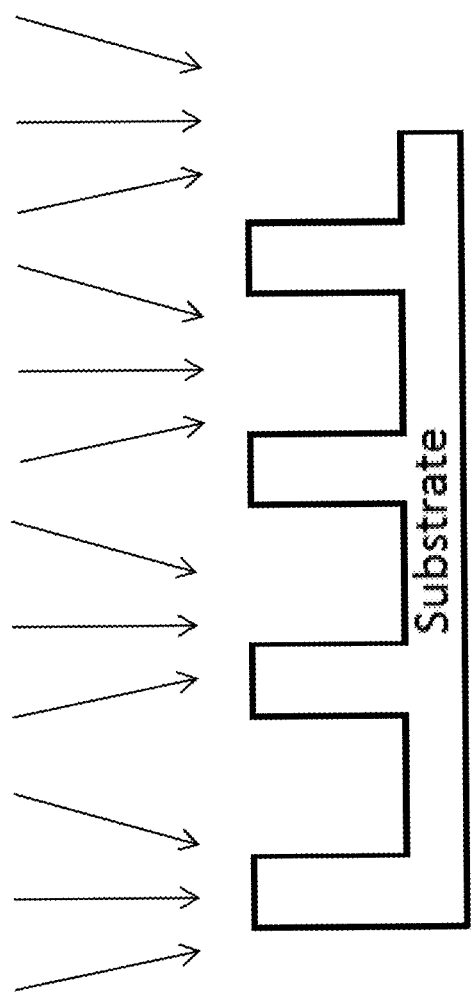

In this way, embodiments of the present disclosure utilize an optimized sputtering deposition of low impedance metals. Typically sputtering involves ejecting a material from a target (which is a source) to the substrate. However, as shown in FIG. 4A, the coverage may also not be complete and continuous since the deposition may be occurring solely from the top of the pillars.

According to embodiments of the present disclosure, the sputtering used in the present disclosure is optimized through the use of special hardware (e.g. a tilting and rotating stage) and high pressure to ensure a complete and continuous coverage over the pillars. In particular, the stage, used to hold the substrate, is able to tilt with respect to the incoming metal being deposited at angles up to 90 degrees (see, FIG. 4B). Additionally, the stage can also rotate at speeds up to 120 r.p.m. A combination of the stage with the high pressure (e.g. 20 mTorr) provides an environment where the metal layer can be provided onto the pillars (and the side of the pillars) in a uniform and controlled manner.

Figure 5:
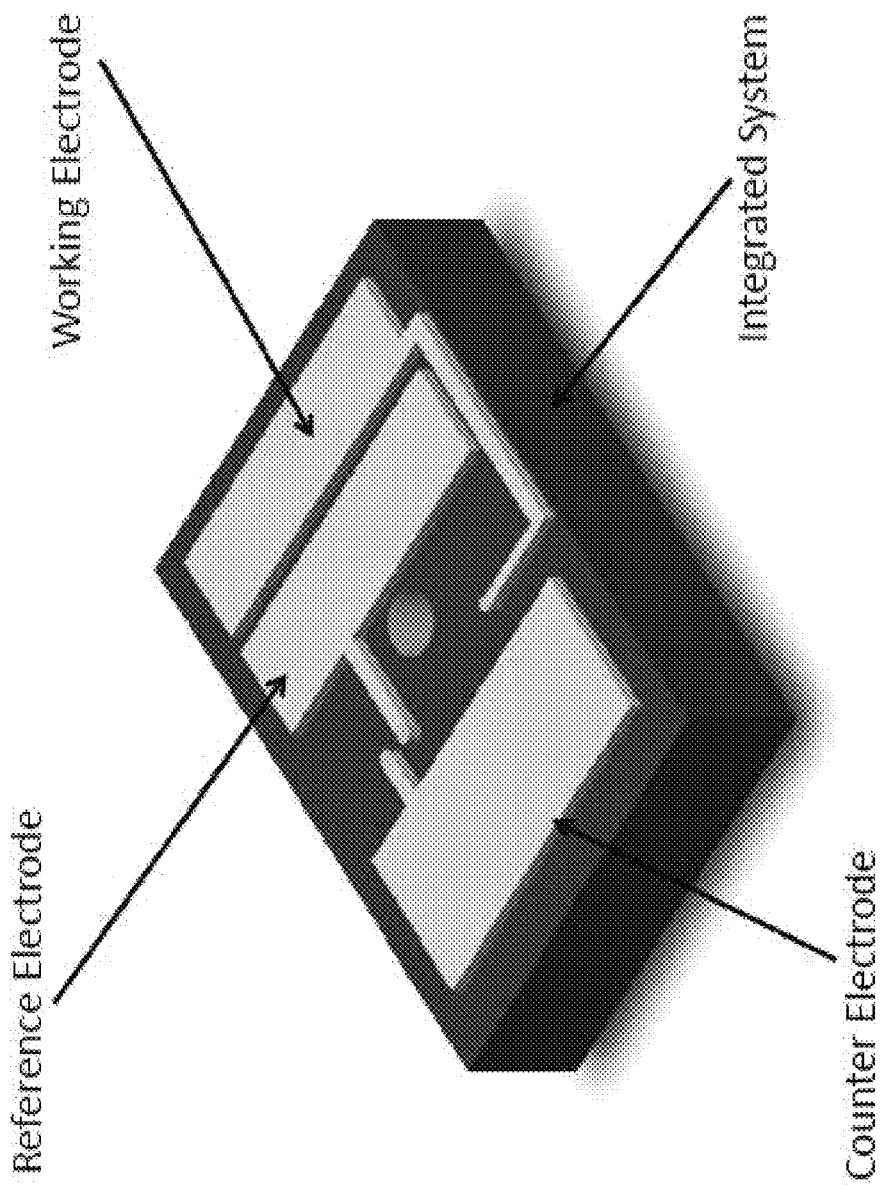
FIG. 5 illustrates an exemplary embodiment of an on-chip electrochemical sensor with three electrodes.

After the metal layer has been deposited, a last step of removing excess metals is performed called liftoff. Liftoff can be performed using image reversal bake and flood exposure methods that are already known in the art. As a result of the methods described above, an electrode is fabricated which can be used in electrode based sensors (e.g. FIG. 5) where the figure illustrates a complete three electrode based sensor.

CMOS Processing

As described above, various substrates (e.g. silicon) can be used for the fabrication of the pillars. It should be noted that the methods for designing and fabricating electrodes are also applicable with CMOS. It should be noted that previous etching on CMOS dies had failed in part because of the challenges associated with etching metals such as difficulties concerning the charges thereof as well as damage to the die in ordinary processes. The invention of the present disclosure overcomes these problems by using masks resistant to degradation by the processes that etch the metal as well as using temperatures of less than 500° C. throughout the entire fabrication process.

As stated above, a benefit of using CMOS is that the CMOS die generally already has insulation present. Therefore, that fabrication step can be skipped.

Figure 6:
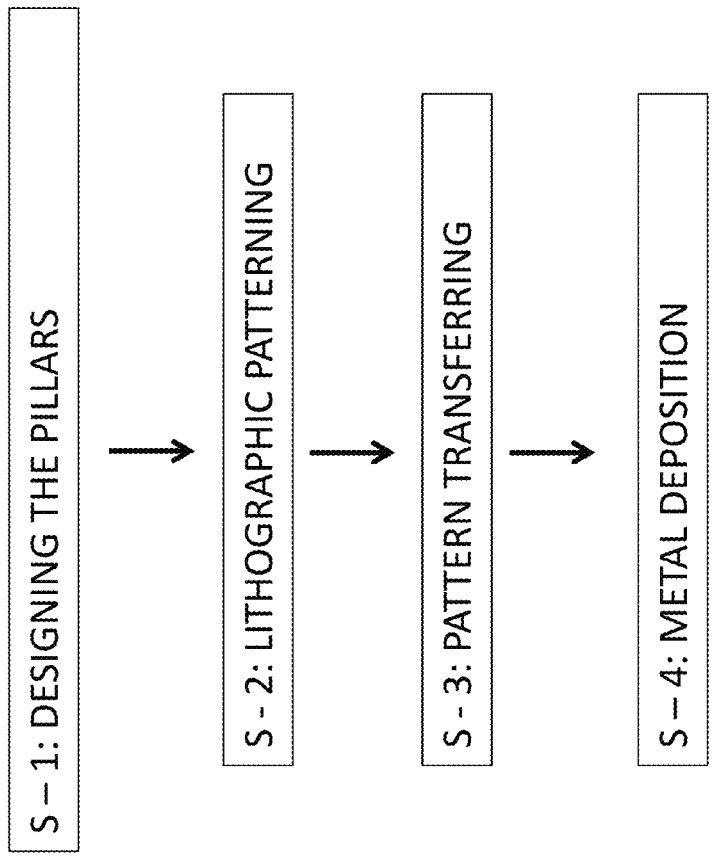
FIG. 6 illustrates a flowchart depicting steps performed in the fabrication method of the present disclosure using CMOS.
Figure 7A:
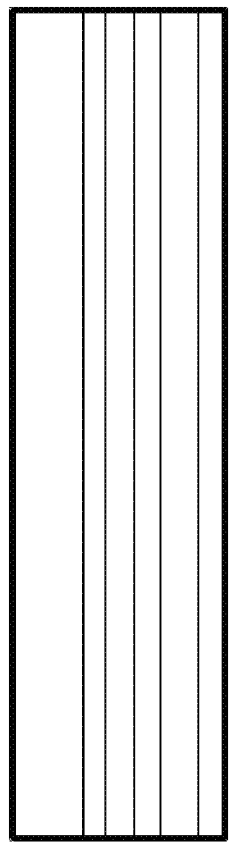
FIGS. 7A-7G illustrate the steps of the fabrication methods using CMOS technology.
Figure 7B:
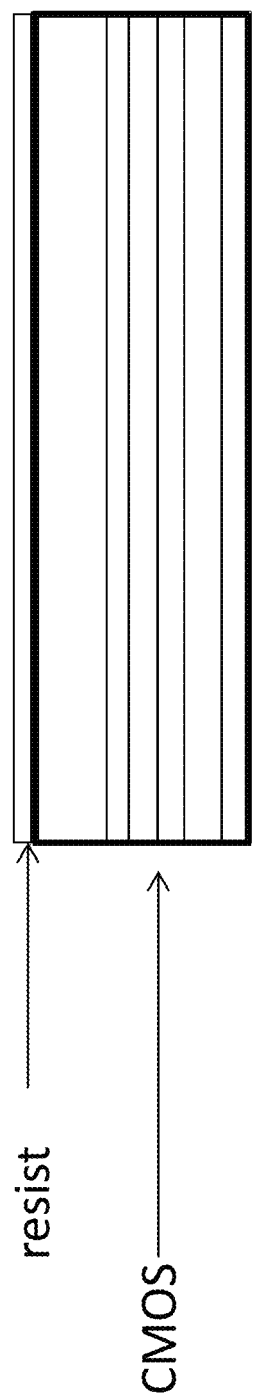
Figure 7C:
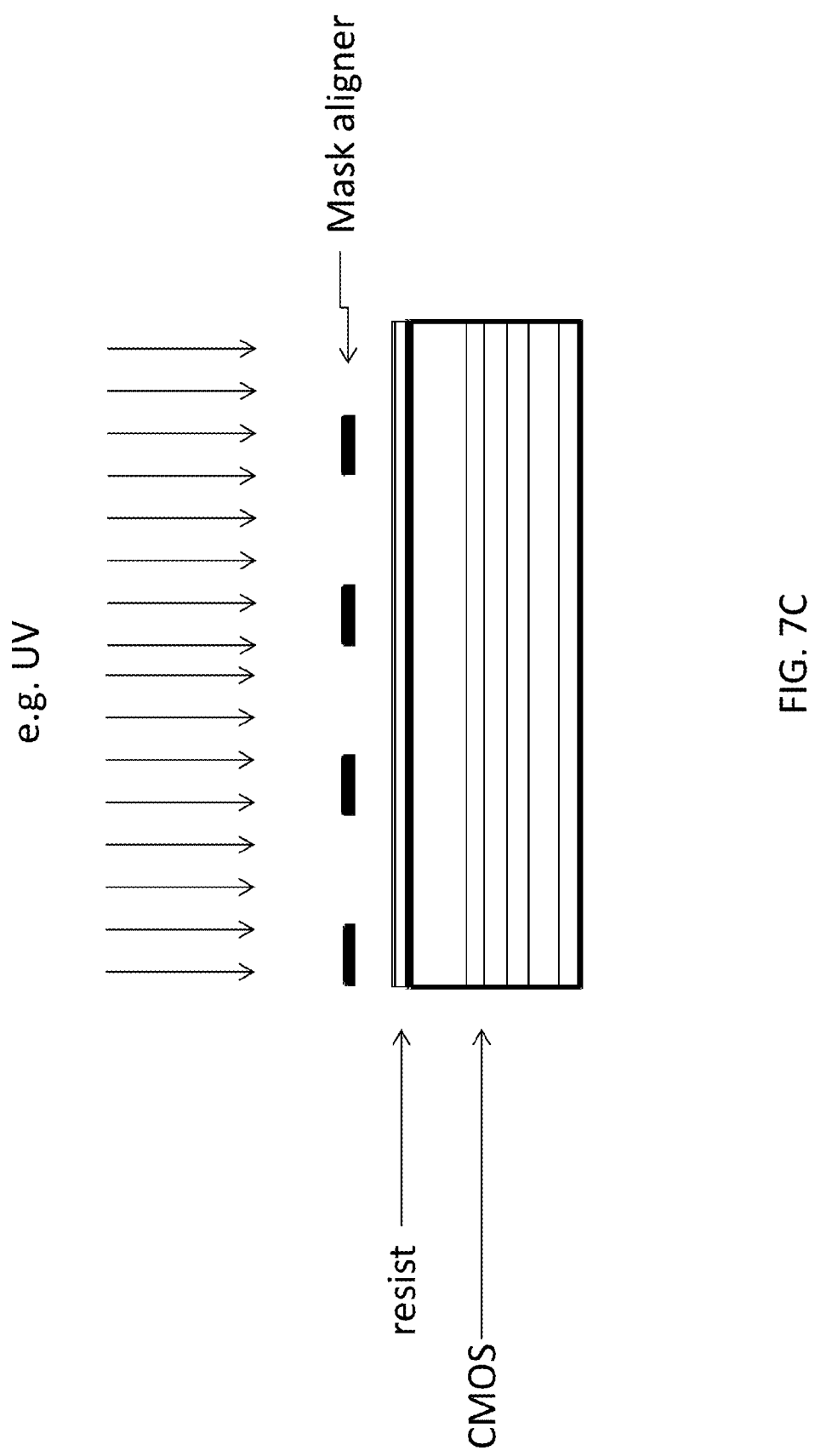
Figure 7D:
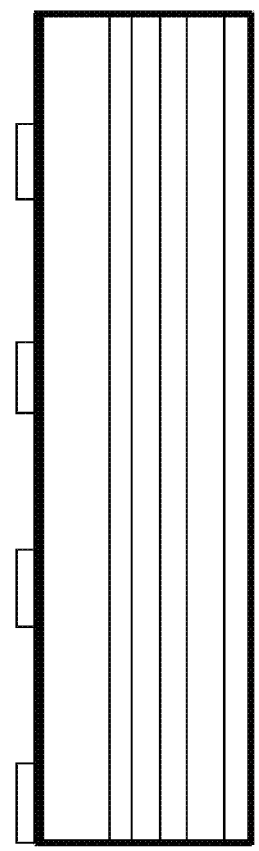
Figure 7E:
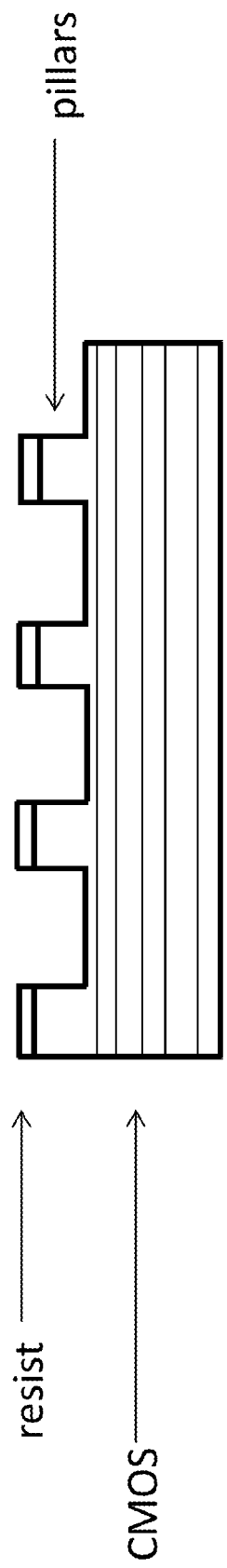
Figure 7F:
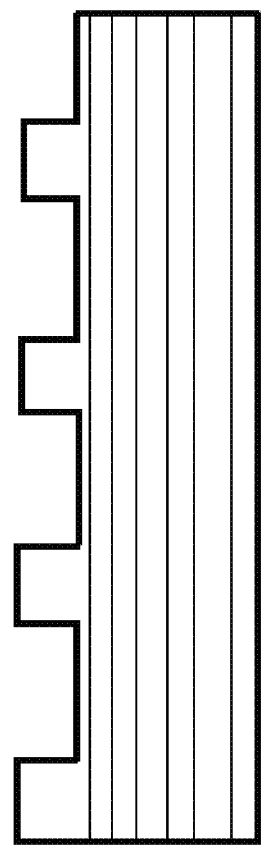
Figure 7G:
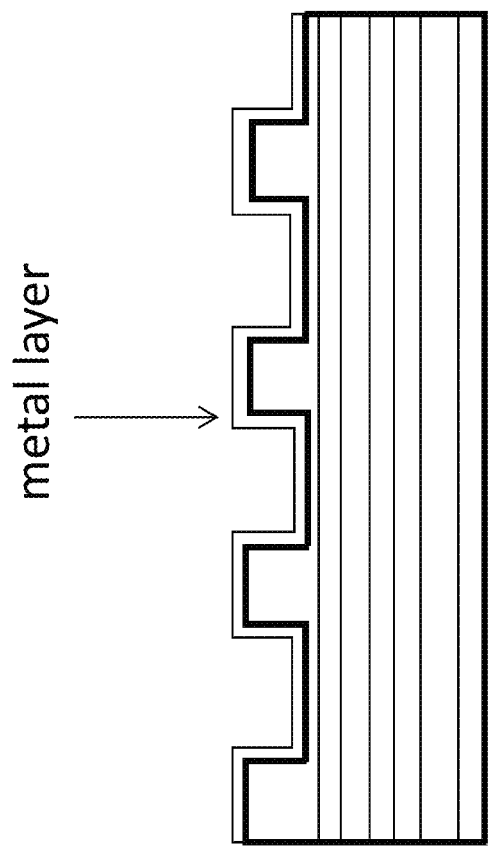

A CMOS die that would be used for embodiments according to the present disclosure is generally a plurality of layers of metals and insulation on a silicon or silicon-on-insulator substrate. Furthermore, the CMOS includes existing elements within its structure. Unlike the fabrication methods described above using a substrate (e.g. silicon) where the entire substrate can be etched, with respect to CMOS, a top most metal layer of the CMOS is designated for the formation of the pillars to be patterned and etched. A flow chart depicting steps performed in the fabrication method of pillars using CMOS can be seen in FIG. 6. Furthermore, FIGS. 7A-7G illustrates the steps of the fabrication method using CMOS.

With fabrication of nanopatterned electrodes using CMOS, extreme temperatures are avoided so as to avoid damaging already existing elements in the CMOS. Such elements being referred to within the CMOS may be underlying structures and/or electronics already imbedded during the fabrication of the CMOS. Thus the use of the room-temperature etching facilitates the aim of avoiding the use of extreme hot or cold temperatures during the fabrication process.

Although the use of CMOS would limit the conditions by which the pillars can be formed, as stated above, there are a number of benefits in adapting the fabrication methods for use with CMOS. First, the use of CMOS can be desired because the pillars formed on the substrate would already be isolated from other pillars. In fact, because of this benefit, the fabrication method described above would not require the use of an insulating material for the pillars (comparing FIG. 1 with FIG. 6). Furthermore, CMOS processes are commercially available and would reduce the overall cost of fabricating the electrodes. Lastly, the elements associated with the CMOS may be adaptable for use after the electrode formation (e.g. electronics) and may be needed for forming a complete integrated sensing platform.

Top-Down and Bottom-Up Hybrid Method of Fabrication

Figure 8:
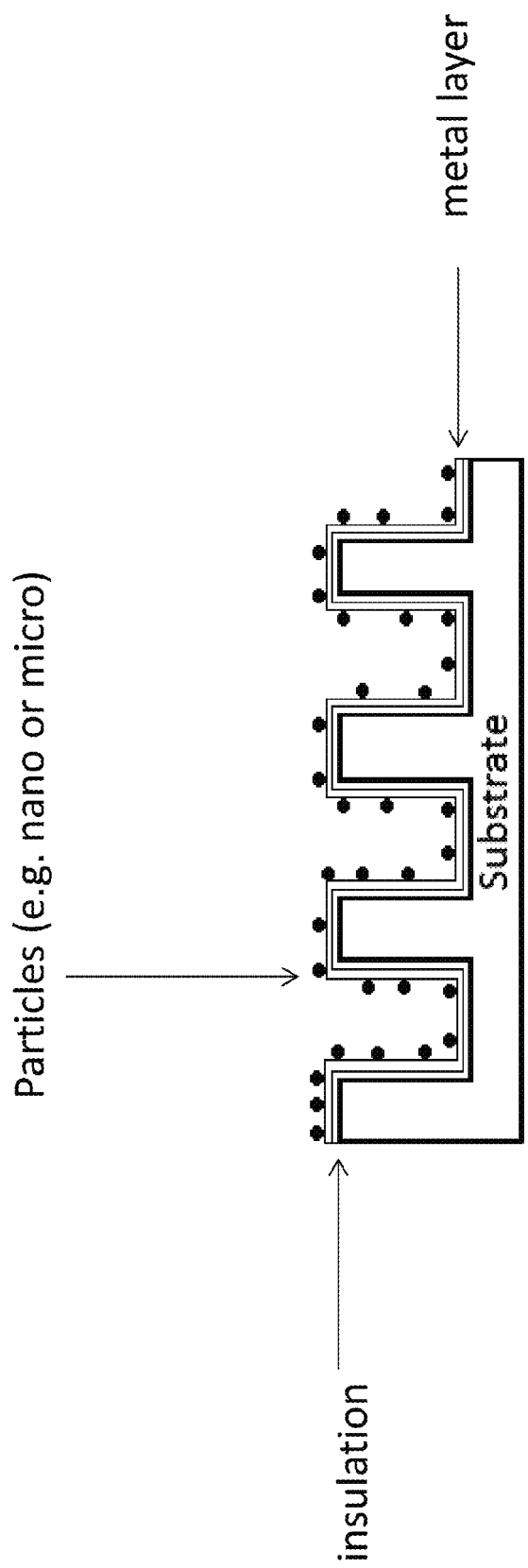
FIG. 8 illustrates a further step associated with the "bottom-up" fabrication method using nano-particles.

As discussed earlier, a number of embodiments according to the present disclosure can be fabricated using a hybrid fabrication method for increased electrode surface area. The hybrid fabrication method first utilizes the steps for top-down fabrication methods of the electrode according to the present disclosure (e.g. steps 1-5 as summarized above) and seen in FIG. 3. However, the additional step which incorporates a "bottom-up" fabrication method is the further use of particles which are deposited onto the pillars after the metal layer has been applied (see, FIG. 8). This step changes the three dimensional structure of the pillar by creating embodiments where bumps and/or deformities exist. The particles can be spun or sprayed onto the pillars. When the solvent is dried, the particles remain on the pillars.

The particles used in the hybrid method are used based on the size of the target element to be detected. For example, if the target species to be detected is a protein, embodiments may use nanoparticles which may be more sensitive. On the other hand, microparticles can also be applied to the pillars for embodiments where the electrode is to be adapted for detecting larger species (e.g. cells).

Embodiments according to the present disclosure may use particles having a size of 10 nm or 1 µm. In various embodiments the particles may be made from platinum.

Examples

The following are descriptions of various embodiments which have been performed using the above methods described in the present disclosure in the fabrication of high surface area electrodes. The results of each of the various embodiments are reviewed under a high power optical microscope or scanning electrode microscope (SEM) in order to determine if such steps are performed properly. Additionally, tests (e.g. measuring impedance) may also be performed to confirm that such structures operate as intended (see, FIGS. 9A-9B).

Figure 9A:
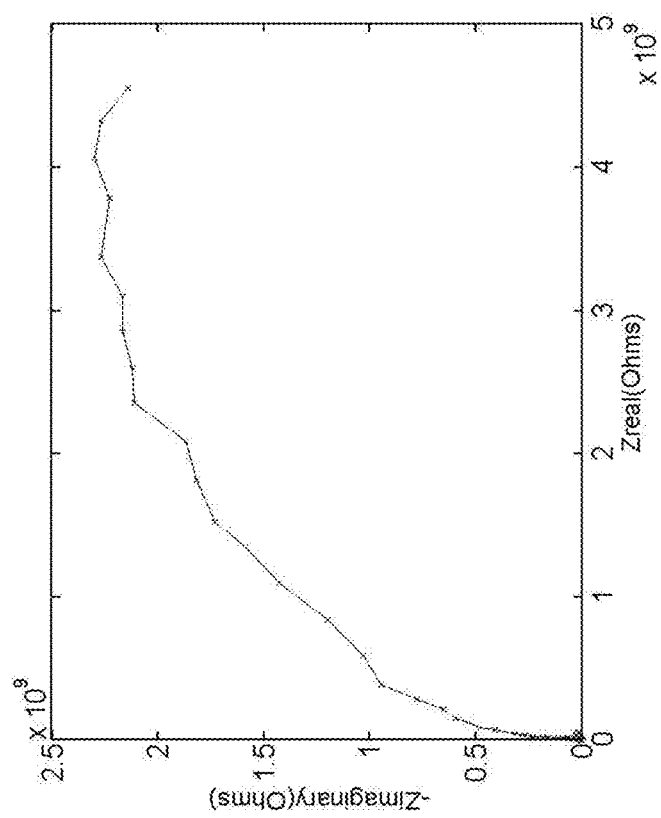
FIGS. 9A and 9B illustrate exemplary test results measuring impedance for fabricated electrodes.
Figure 9B:
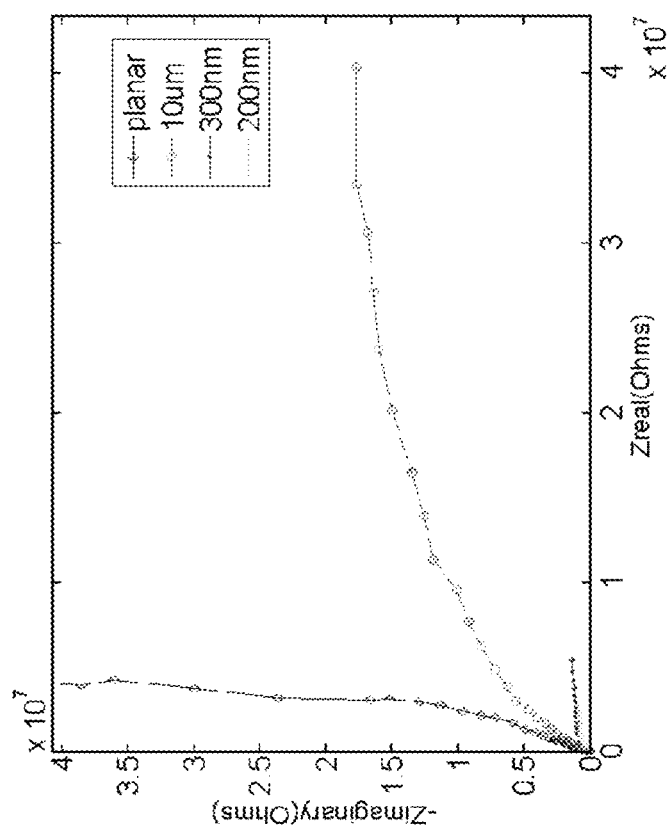

With reference to FIGS. 9A and 9B, impedances of the electrodes are measured using frequency ranging from 0.01 Hz to 1 MHz. This impedance is obtained by placing the electrodes in a buffer solution (e.g. PBS) and using a potentiostat to take the measurements. In particular, with reference to FIG. 9B, a zoomed in portion of impedance measurements comparing the impedances of different scaling of pillars is provided on the same graph.

It was noted that the electrodes have impedance levels similar to an electrical circuit having a capacitor and resistor in parallel. Thus, by reviewing the impedances of other fabricated electrodes, determination of whether or not they were fabricated properly can be confirmed using this method.

Example 1

Silicon and CMOS Micro-Scale Patterning

In order to test micro-scale patterning for embodiments of the present disclosure, the following set up was used. First, a Carl-Suss MA6 mask aligner was used for optical lithography. For patterned electrodes, non-contact (proximity mode) lithography was used to avoid damage to small structures. AZ5214E photoresist was used for micro-scale patterning. An inward tapered profile was achieved for better lift-off performance by using image reversal processing. The resist was spun at 4000 rpm for 1 minute and baked at 95° C. for 4 minutes. UV exposure was done using the mask aligner for 2 seconds using an intensity of 15 mW/cm$^2$. Following the UV exposure, an image reversal bake at 110° C. for 2 minutes and a flood exposure for 10 seconds was performed. The pattern was then developed using MF-319 for a minute. Successful patterning was confirmed by optical microscopy (not shown).

Example 2

Silicon and CMOS Nano-Scale Patterning

In order to test nano-scale patterning for embodiments of the present disclosure, the following set up was used. First, PMMA 950 A4 was used to achieve clean lift-off while still achieving a desired resolution. The resist was spun at 4000 rpm for 1 minute followed by a 180° C. bake for 5 minutes. Next, a dose of 1200 μc/cm$^2$ was used to write the pattern in a Leica EBPG5000+ system. Patterns were developed in 1:3 solution of MIBK and IPA for 20 seconds followed by a deionized water rinse. Afterwards, a 50 nm alumina mask was sputter coated in a Temescal TES BJD-1800 DC reactive sputter system by depositing aluminum in oxygen plasma for 5 minutes. Lastly, mask liftoff was performed in dicholoromethane in an ultrasonic bath for 2 minutes. Successful patterning was confirmed by optical microscopy (not shown).

Example 3

Silicon Etching

In order to test silicon etching for embodiments of the present disclosure, the following set up was used. In the embodiment shown, a room-temperature silicon plasma etch was used with the nano-scale features.

Aluminum oxide was deposited on the patterned silicon with a TES 1800 DC magnetron system, using a 99.995% aluminum target and a 5:1 mixture of argon to oxygen as the process gas. This ratio of gases allows for the aluminum to be sputtered without poisoning the target while still deposits a stoichiometric aluminum oxide. At 400 W DC power, this process deposited alumina at an approximate rate of 10 nm min$^{-1}$. Liftoff is carried out in acetone for the micron scale and a mixture of acetone and dichloromethane for the nanoscale pattern.

Etching was performed using Oxford Instrument's PlasmaLab System 100 ICP-RIE 380s with a Pseudo-Bosch etch. Etching was performed at 15 degrees Celsius. An ICP power of 1300 Watts combined with a RIE power of 23 Watts in a Chamber Pressure of 10, SF$_6$ flow rate of 32 SCCM, and C$_4$F$_8$ flow rate of 53 SCCM was found to provide control.

Figure 10A:
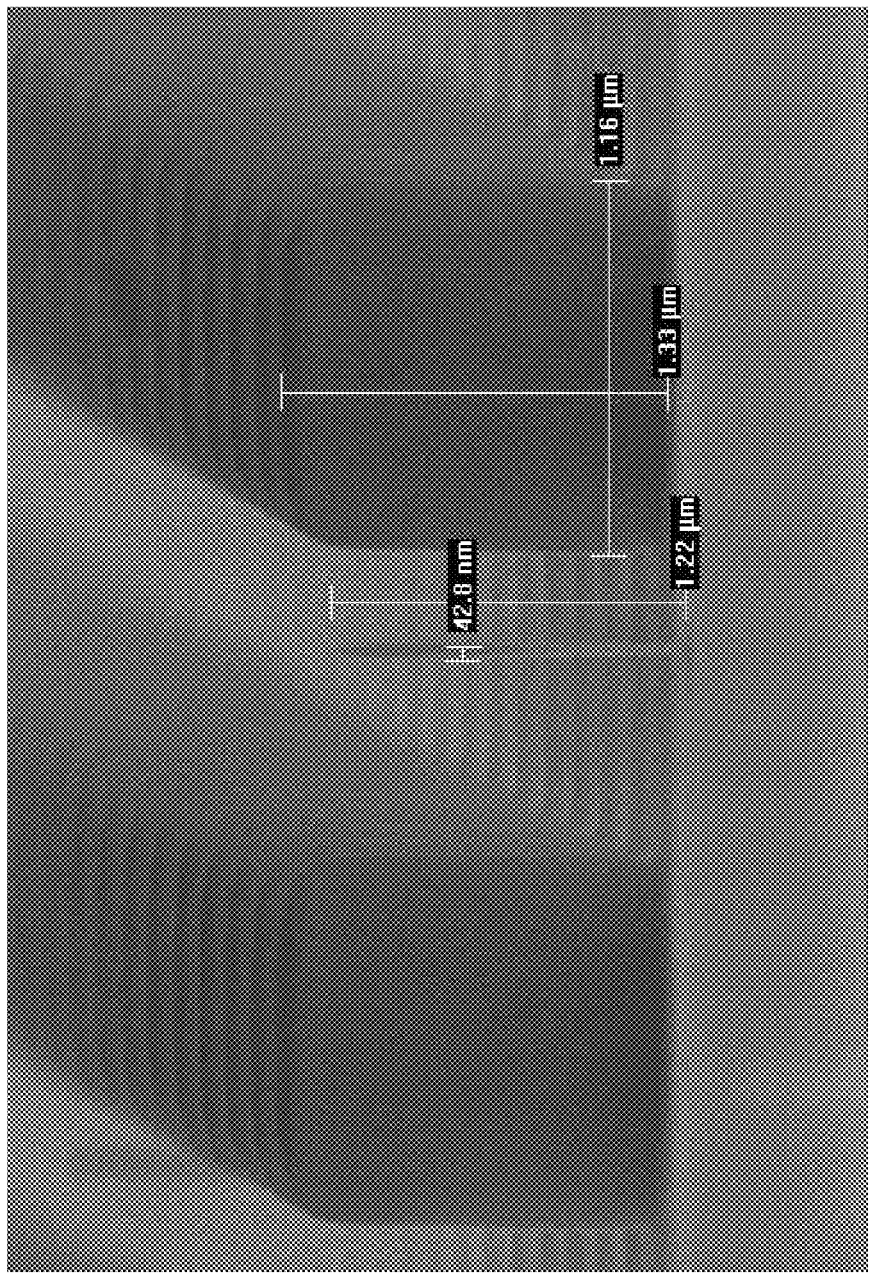
FIGS. 10A and 10B illustrate exemplary embodiments of a SEM image of plasma-etched pillars in both 1 μm diameter silicon pillars with ~50 nm pillar for comparison.
Figure 10B:
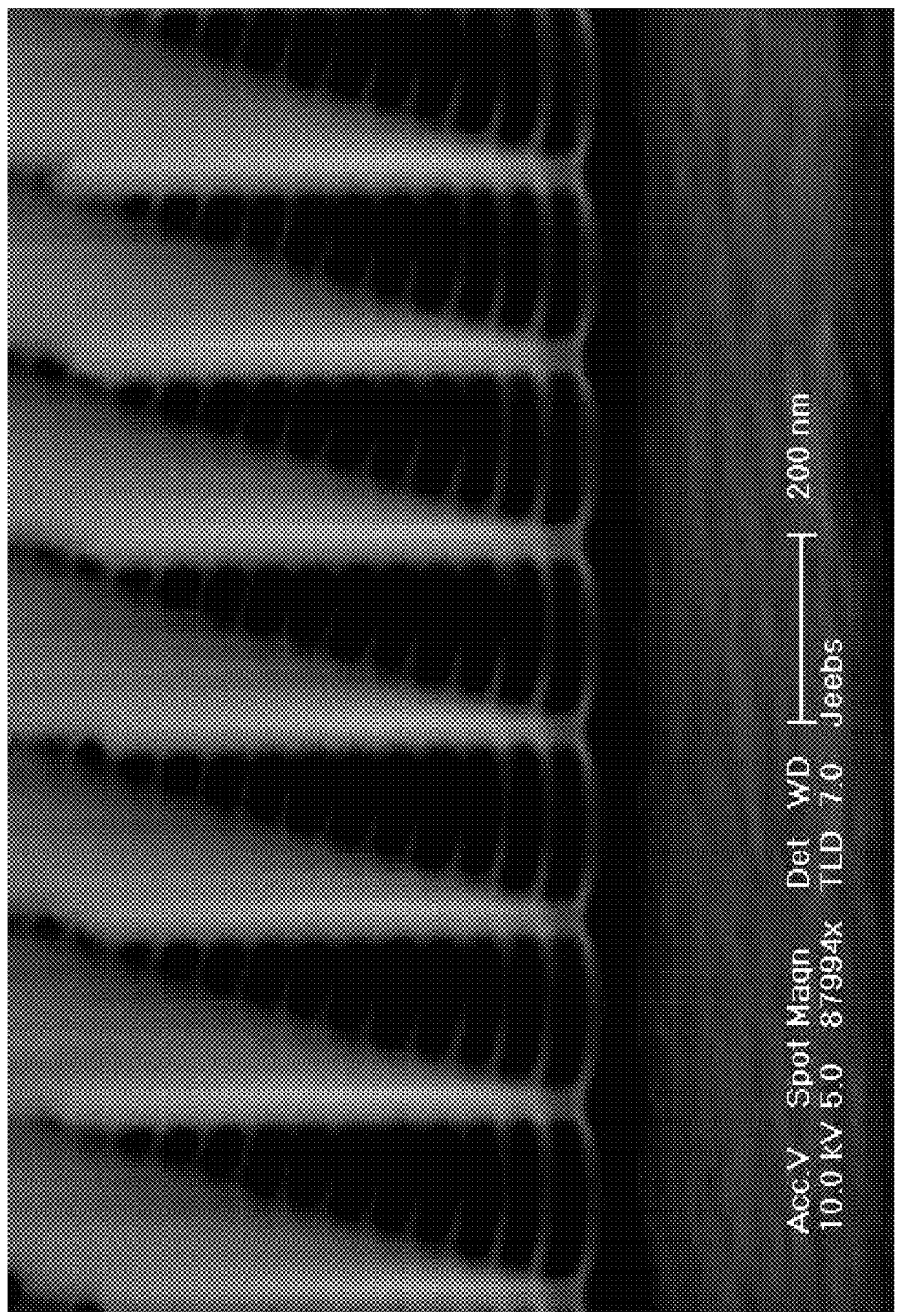

The silicon plasma etch is optimized to achieve uniform etch depth for all pillar widths and uniform sidewall roughness. A benefit of such uniformity allows reliable comparison between performances of electrodes with different sized pillars. A resulting embodiment according to the present disclosure using the above procedure can be seen in FIGS. 10A and 10B. Success can be seen in the dimensions and uniformity of the formed structure.

Example 4

CMOS Etching

In order to test silicon etching for embodiments of the present disclosure, the following set up was used. The patterning was performed with a MA-N 2403 resist. Pillars were fabricated using both dry plasma (Cl$_2$:BCl$_3$) as well as wet etchants (e.g. TMAH) to etch away parts of the metal pad using a UNAXIS RIE machine. For the dry plasma (Cl$_2$:BCl$_3$) etch the temperature was set to 25 degrees Celsius and RIE power to 120 watts. Flow rate for Cl$_2$ was set to 4 SCCM and the flow rate of BCl$_3$ was set to 20 SCCM.

For the wet TMAH etch the surface was submerged in a liquid for room temperature for 10 minutes.

Figure 11:
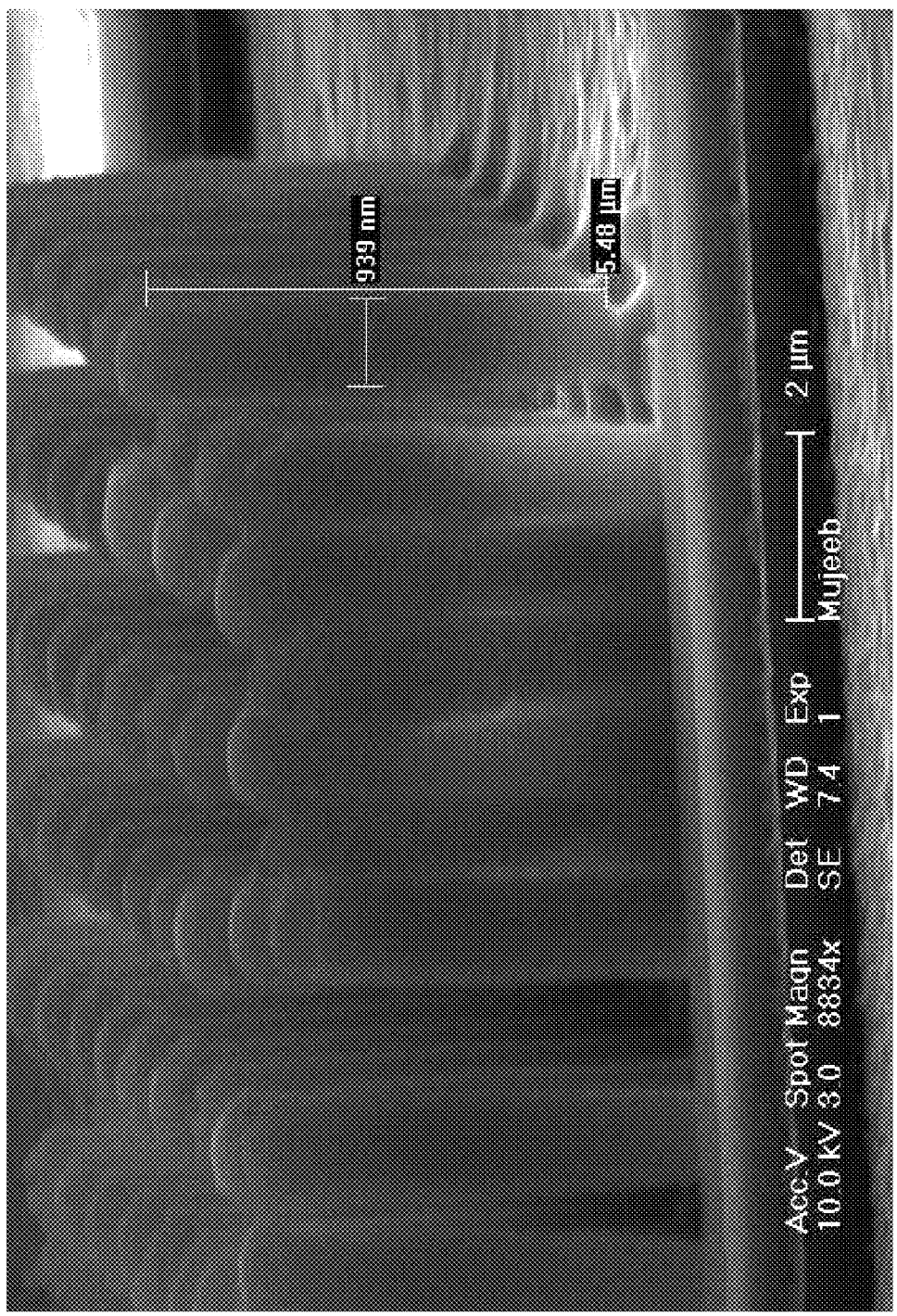
FIG. 11 illustrates an exemplary embodiment of pillars etched in CMOS aluminum pad.
Figure 12A:
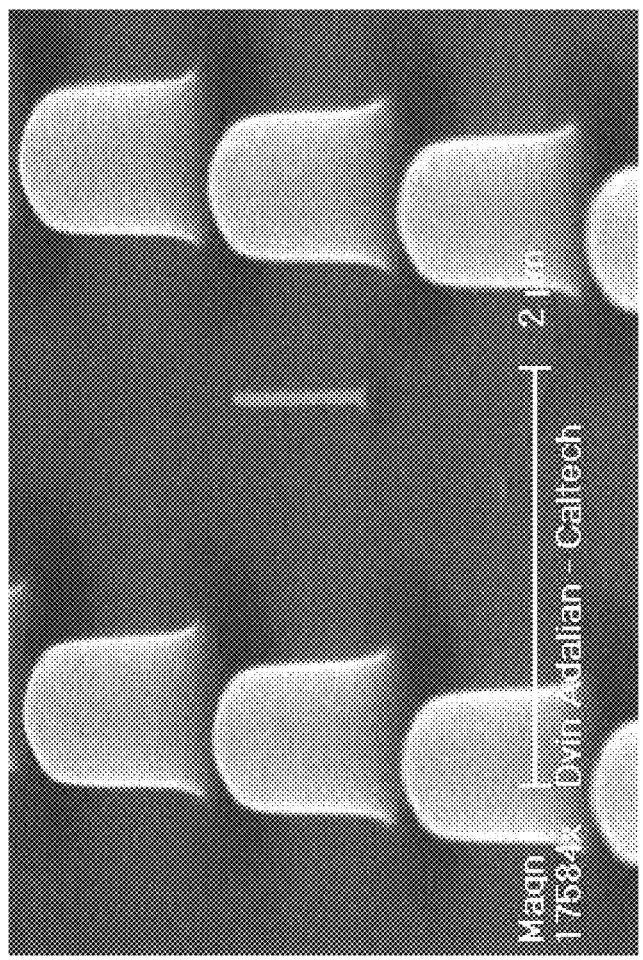
FIGS. 12A-12D illustrate exemplary embodiments of pillars after thermal oxidation, stability of the arrays after oxidation as well as high voltage imaging to confirm the conformity of the oxide layer.
Figure 12B:
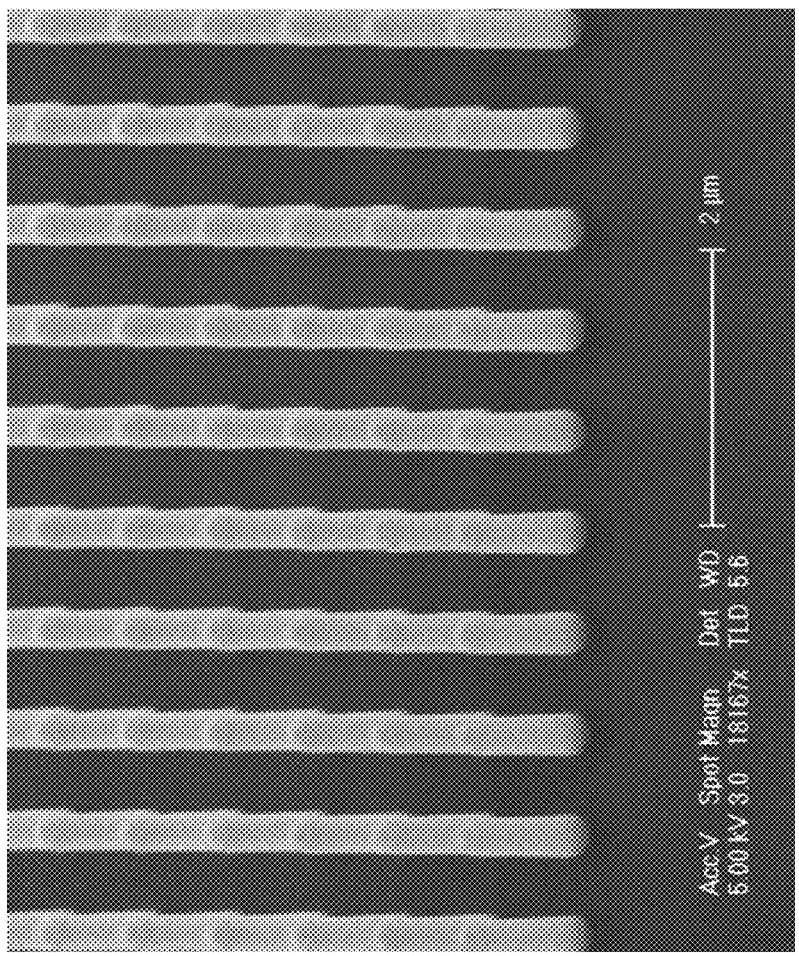
Figure 12C:
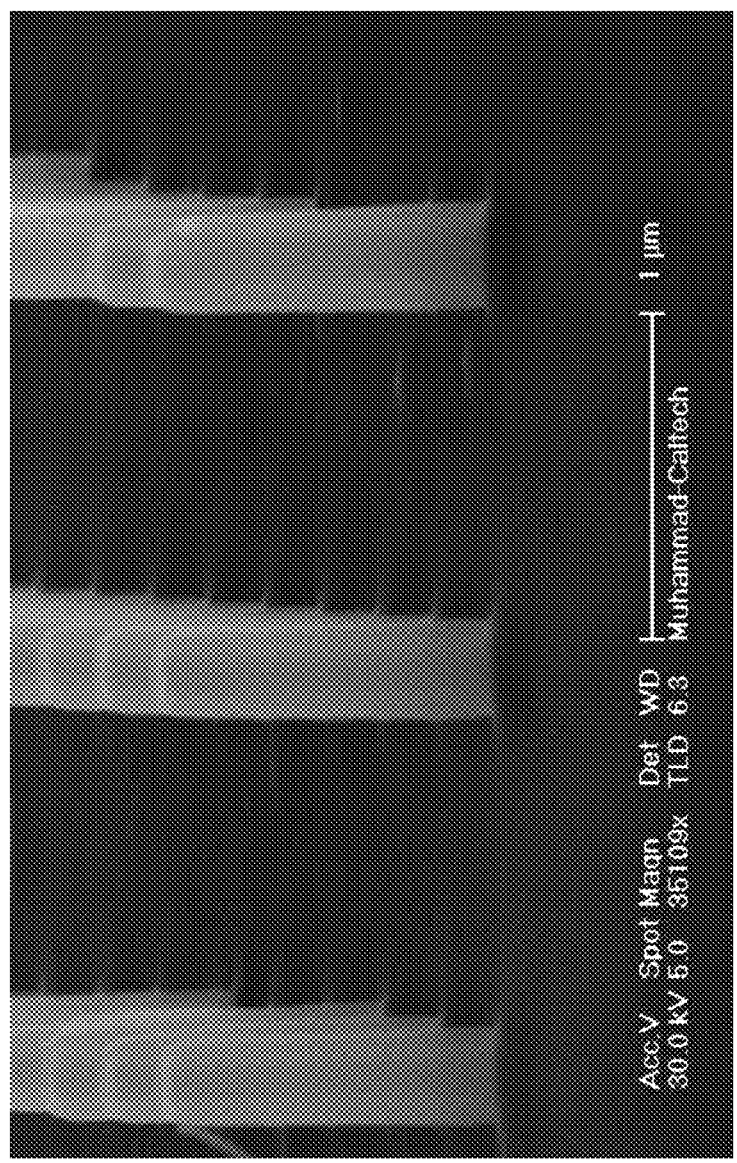
Figure 12D:
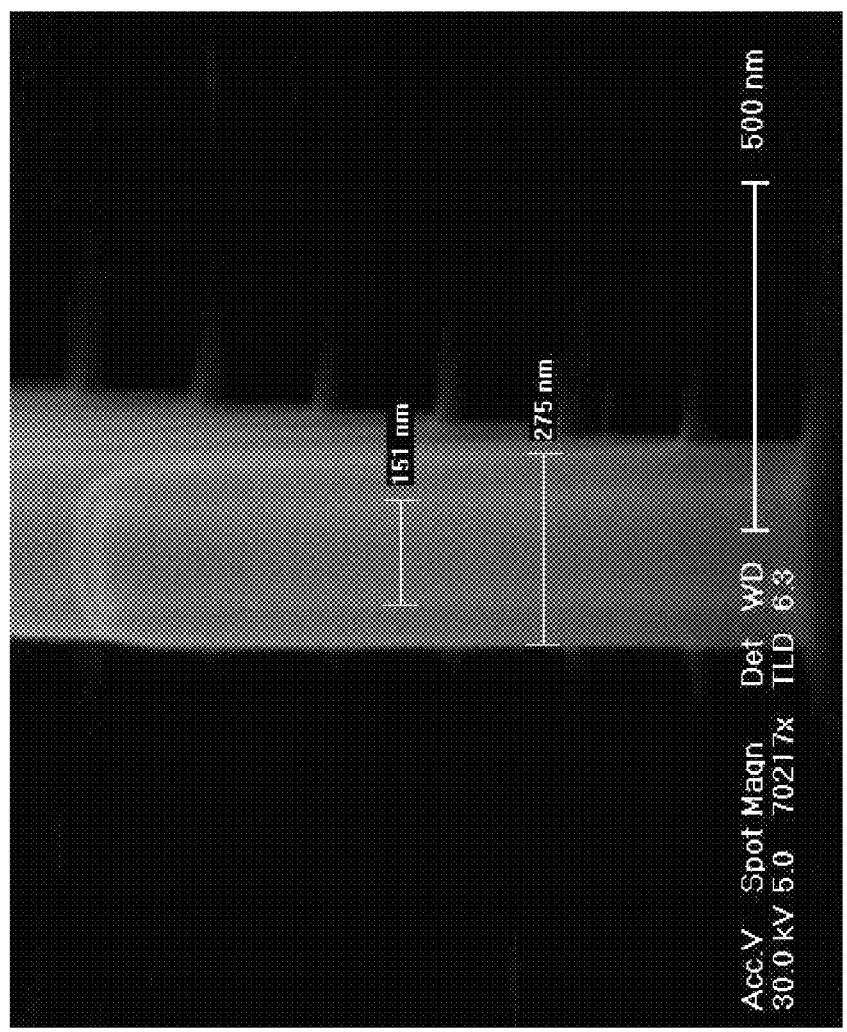
Figure 13A:
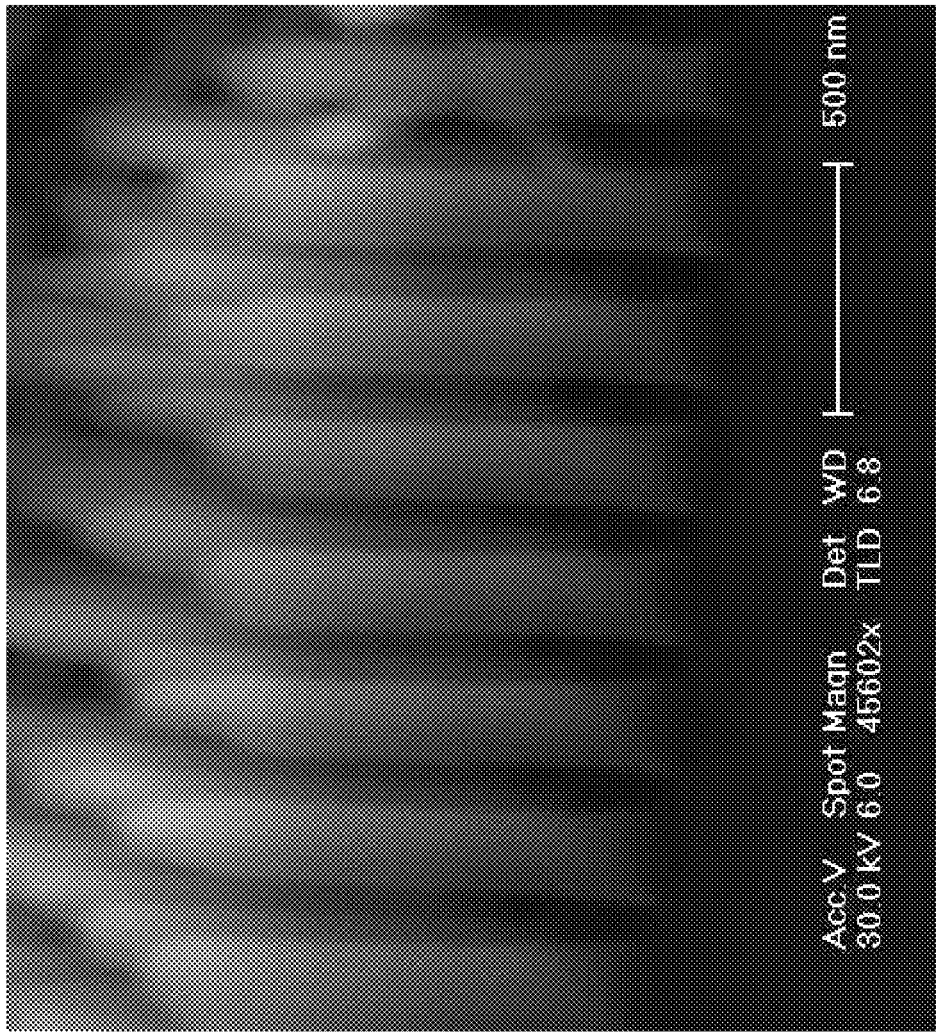
FIGS. 13A-13C illustrate exemplary embodiments of pillars after PECVD passivation coating after a 30 second and 1 minute of deposition and detailed view of the thin deposition, respectively.
Figure 13B:
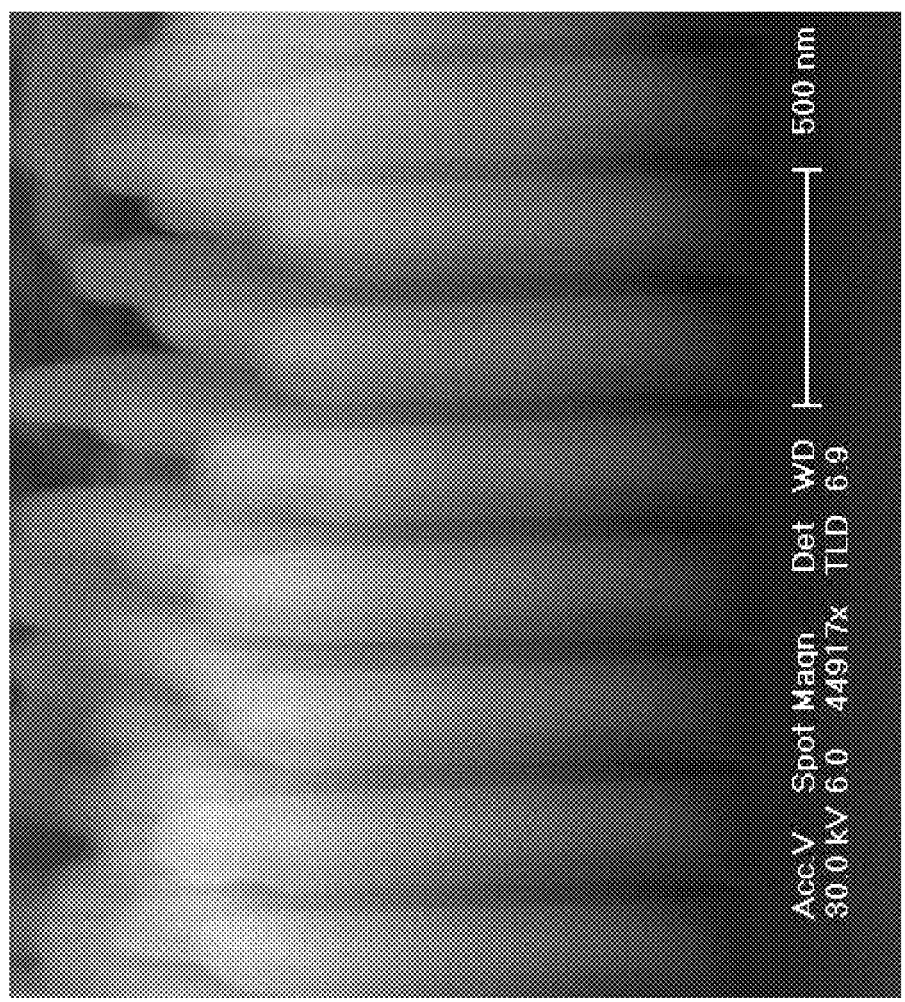
Figure 13C:
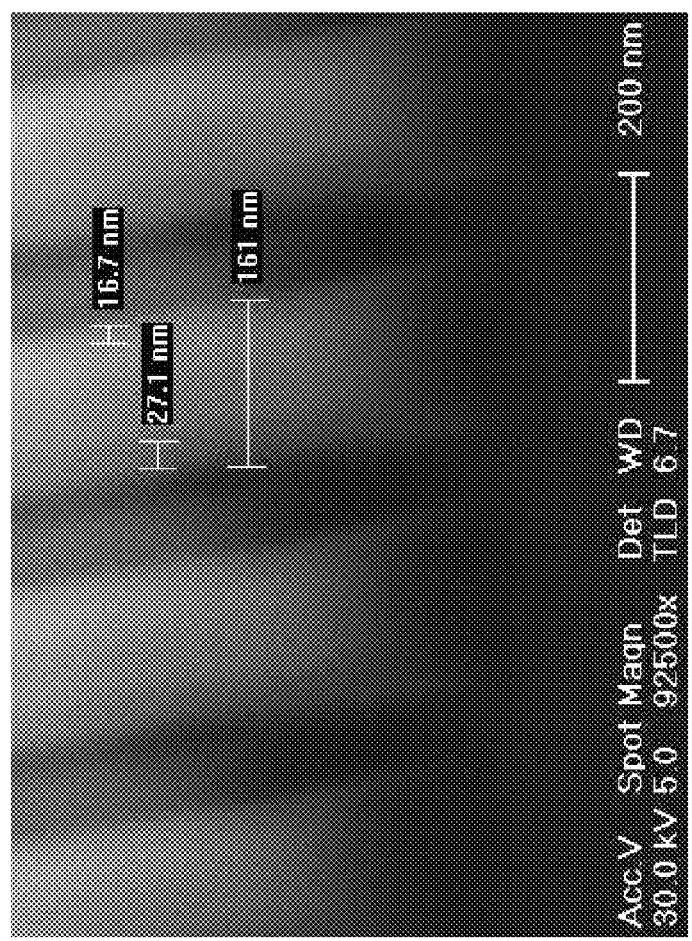

A resulting embodiment according to the present disclosure using the above procedure can be seen in FIG. 11. Success can be seen in the dimensions and uniformity of the formed structure.

Example 5

Thermal Silicon Oxidization

In order to test silicon oxidation for embodiments of the present disclosure, the following set up was used. First, pillar structures were oxidized in a wafer furnace at 1000° C. for 90 minutes, followed by 15 minute nitrogen anneal and a gradual return to room temperature.

A resulting embodiment according to the present disclosure using the above procedure can be seen in FIGS. 12A-12D. It should be noted that the silicon core and the outer silicon oxide layer can be differentiated due to the electron-beam imaging transparency and contrast.

Success can be seen be checked by reference to a color chart, visual observation of surface, and SEM images of pillars.

Example 6

Low Temperature Silicon Oxidization

In order to test low temperature silicon oxidization for embodiments of the present disclosure, the following set up was used. First, an Oxford HD ICP-CVD system was used to perform plasma enhanced chemical vapor deposition (PECVD) of silicon oxide layers. Operating parameters for the system were 350° C. table temperature and silicon oxide deposition rate of ~70 nm/minute at high pressure (~1000 mTorr). A resulting embodiment according to the present disclosure using the above procedure can be seen in FIGS.

13A-13C. The oxide layer has insulating properties (which was tested using two point electrical measurements).

Example 7

Metal Deposition—Electron Beam Evaporation

Figure 14A:
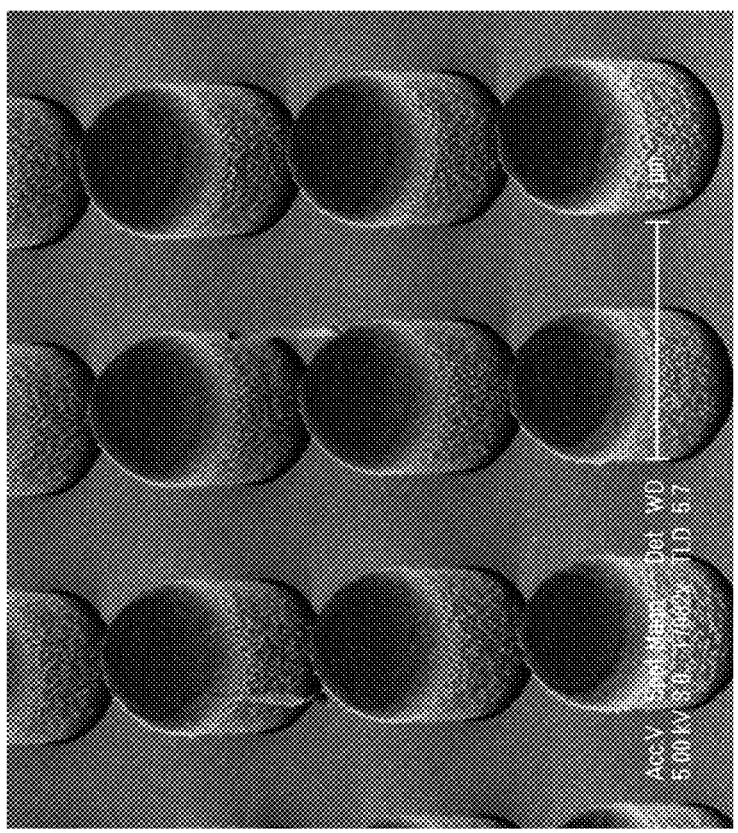
FIGS. 14A and 14B illustrate exemplary embodiments of pillars after electron beam evaporation of the metal coating and a close up of one of the pillars, respectively.
Figure 14B:
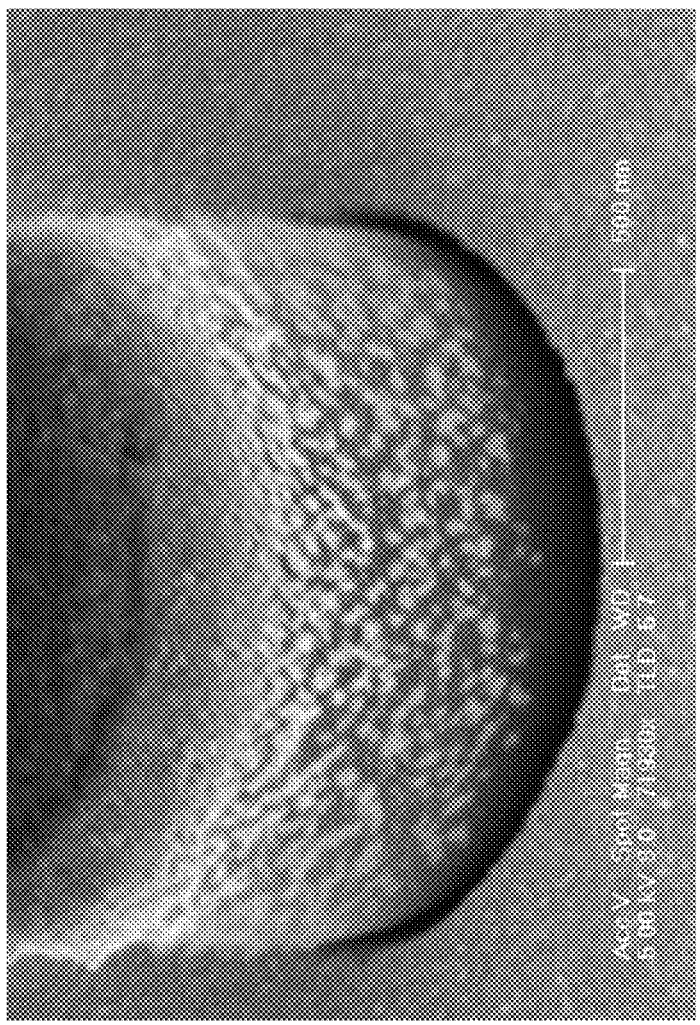
Figure 15A:
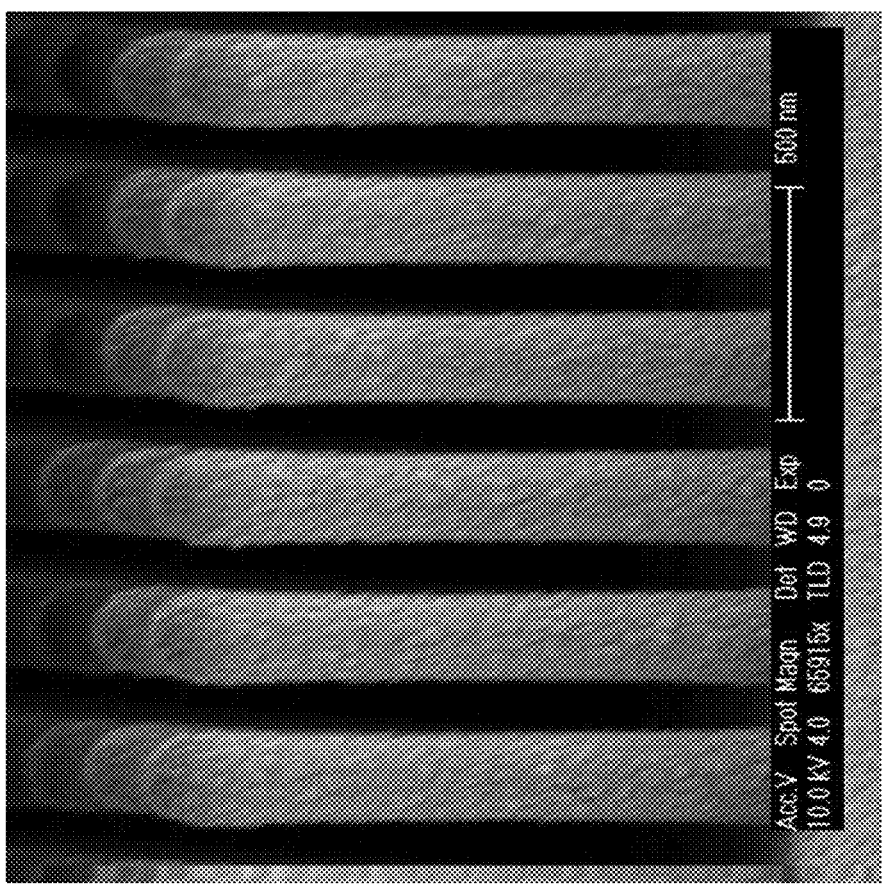
FIGS. 15A and 15 B illustrate exemplary embodiments of coating the pillars after sputter coating by silver.
Figure 15B:
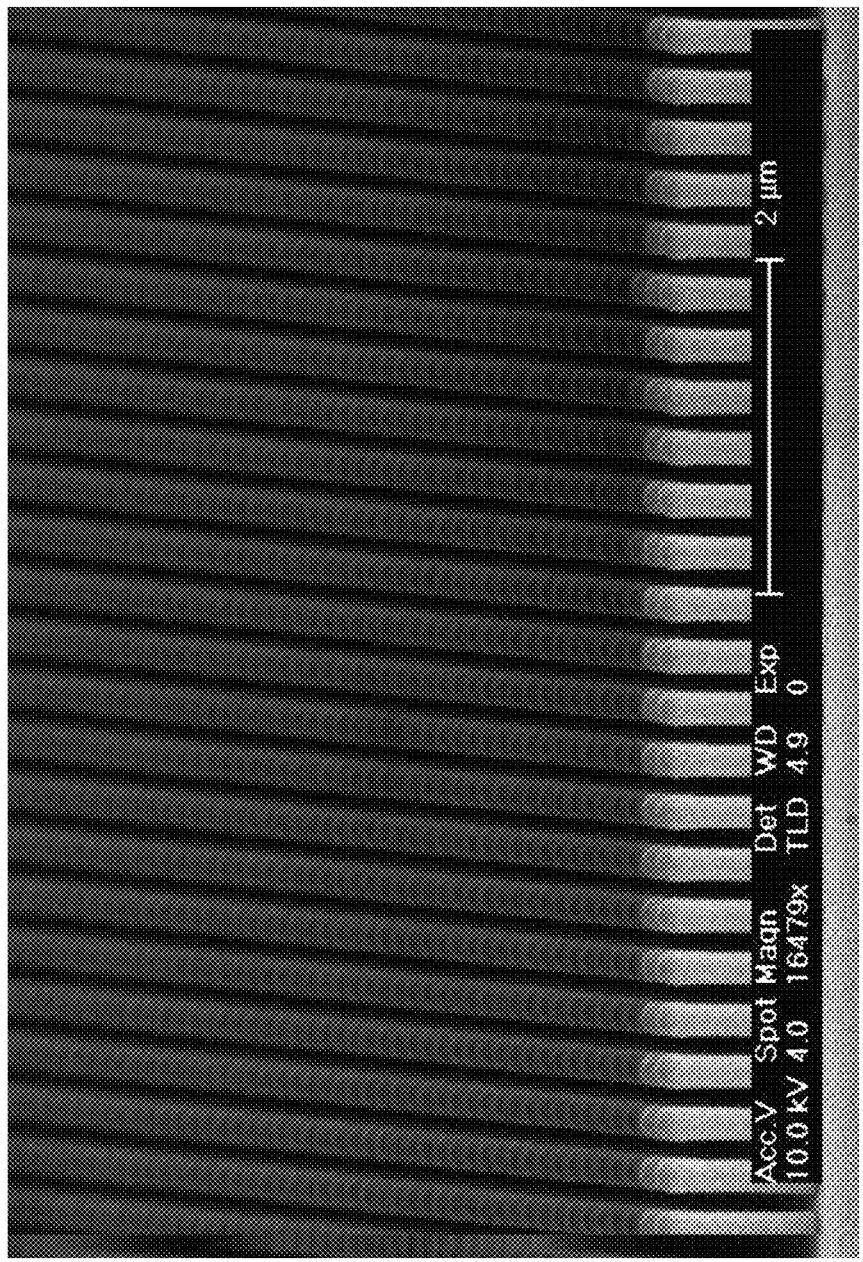
Figure 16A:
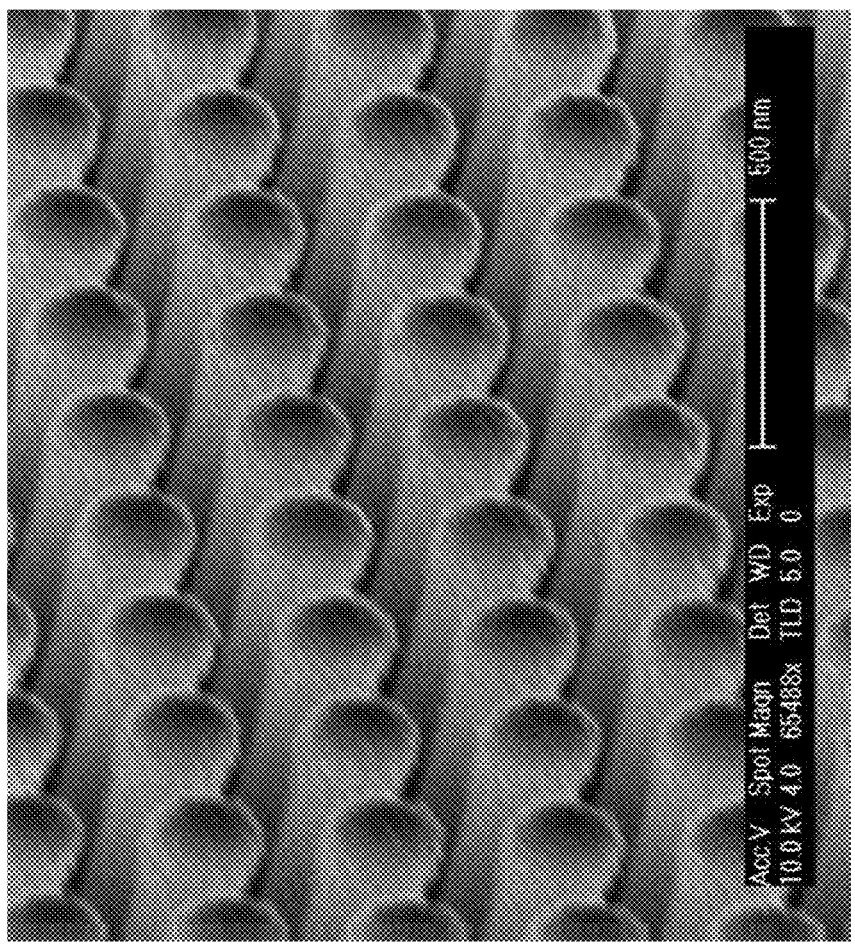
FIGS. 16A and 16B illustrate exemplary embodiments of SEM confirmation of the metal coating.
Figure 16B:
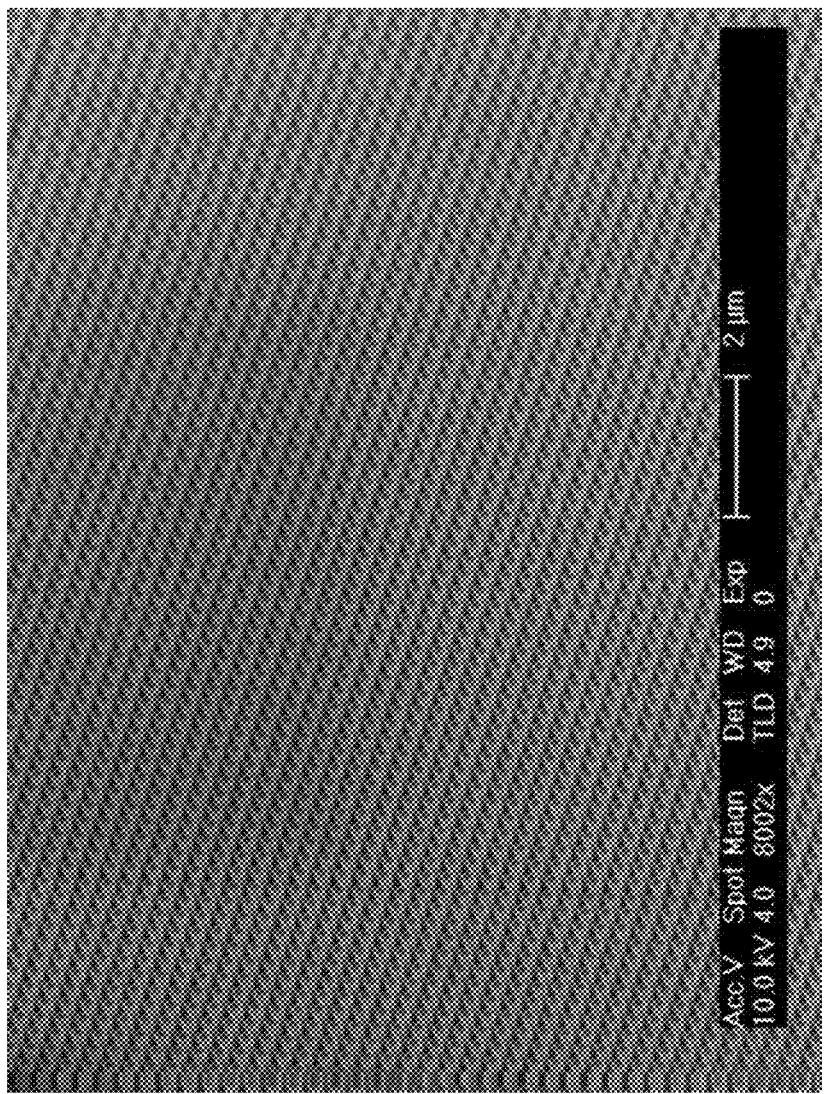
Figure 17A:
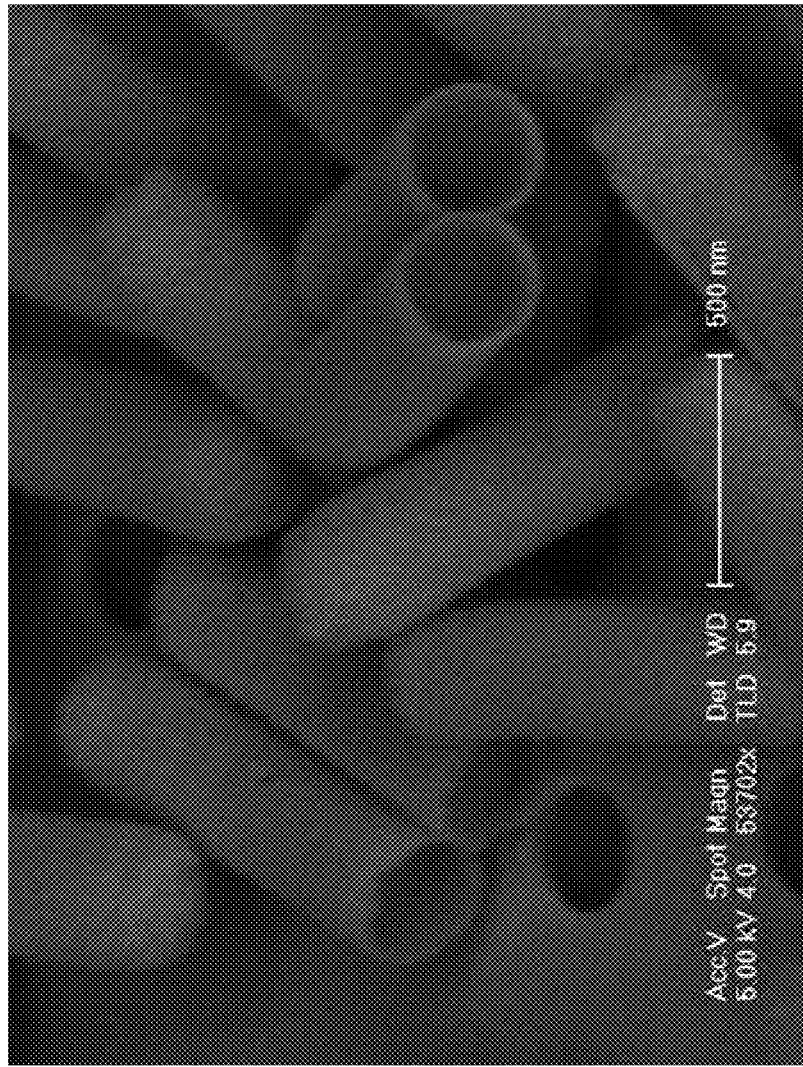
FIGS. 17A and 17B illustrate exemplary embodiments of contiguous coating of an entire pillar.
Figure 17B:
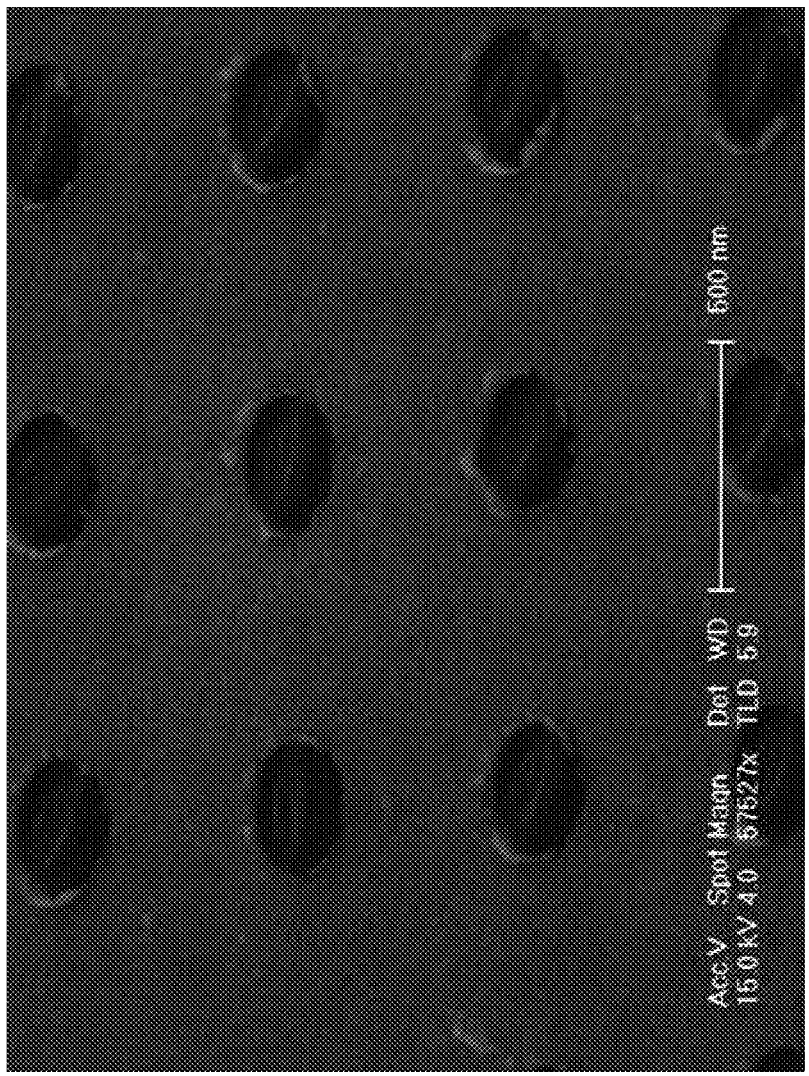

In order to test metal deposition electron beam evaporation deposition for embodiments of the present disclosure, the following set up was used. First, deposition was performed on a CHA electron beam deposition system at $2 \times 10^{-6}$ torr. The sample substrate was placed on a rotating stage and various low impedance metals such as Au and Pt were used as metal sources. A 5 nm Ti adhesion layer was evaporated at 0.5 angstrom/s and subsequently an Au or Pt layer of 50 nm or 100 nm was evaporated at 1 angstrom/s. Results show that it may be difficult to realize conformal coating on these pillars using electron beam deposition because of the inherent straight line deposition mechanism in these systems. A resulting embodiment according to the present disclosure using the above procedure can be seen in FIGS. 14A and 14 B. Note how the pillars do not appear to be uniformly covered with covering concentrated near the top of the pillar and the top of the side wall of the pillar. Near the base of the pillar as seen in FIG. 14B there is a lack of coverage Example 8

Metal Deposition—Sputter Deposition

In order to test metal deposition sputter deposition of low impedance metals for embodiments of the present disclosure, the following set up was used. Metal deposition sputter deposition can be used to perform conformal coatings. First high density Argon plasma of 20 mTorr is used to increase the isotropy of the deposition. A 5 nm Ti adhesion layer is DC sputtered and then 50 nm or 100 nm Au or Pt films were DC sputtered. Resulting embodiments according to the present disclosure using the above procedure can be seen in FIGS. 15A, 15B, 16A, 16B, 17A and 17B.

A special stage was used which could tilt the sample with respect to the incoming metal atoms at angles up to 90° C. Secondly, the stage could rotate at speeds up to 120 r.p.m. A combination of tilt and rotation along with optimization of plasma parameters (high pressure, around 20 mTorr) resulted in very uniformly controlled conformal sidewalls.

Example 9

Metal Deposition—Ion Beam Induced Deposition

Figure 18A:
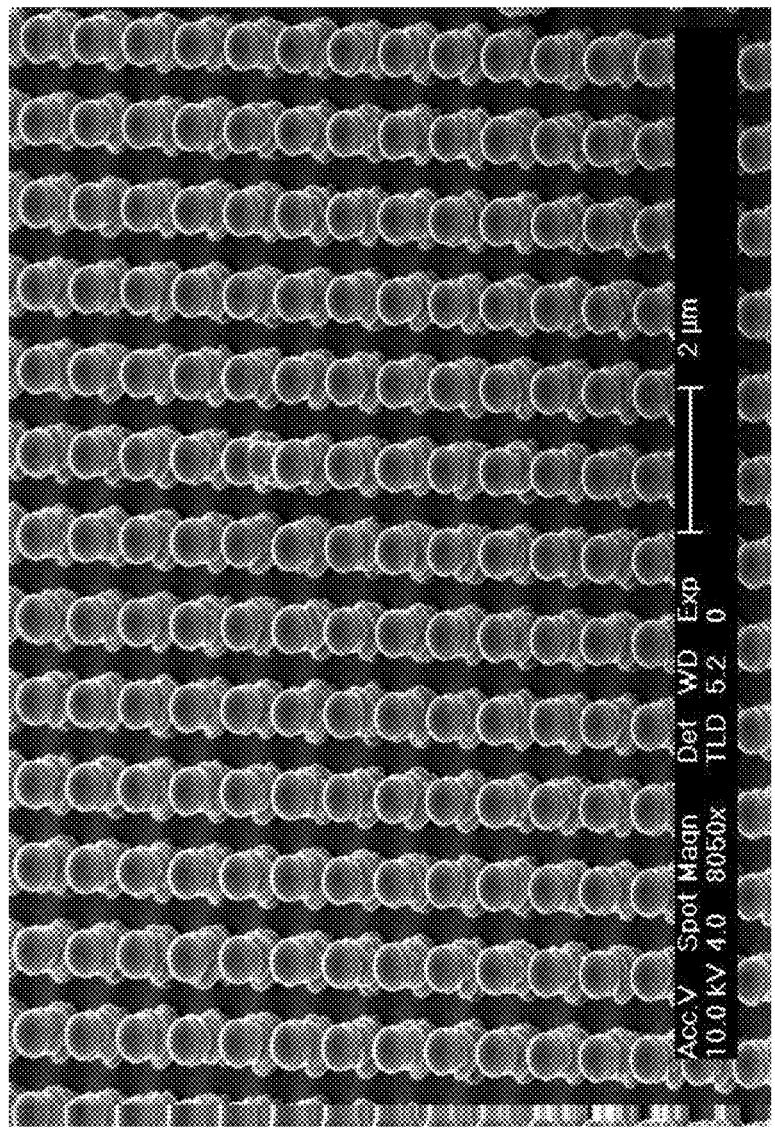
FIGS. 18A and 18B illustrate exemplary embodiments of pillars after ion beam induced metal coating.
Figure 18B:
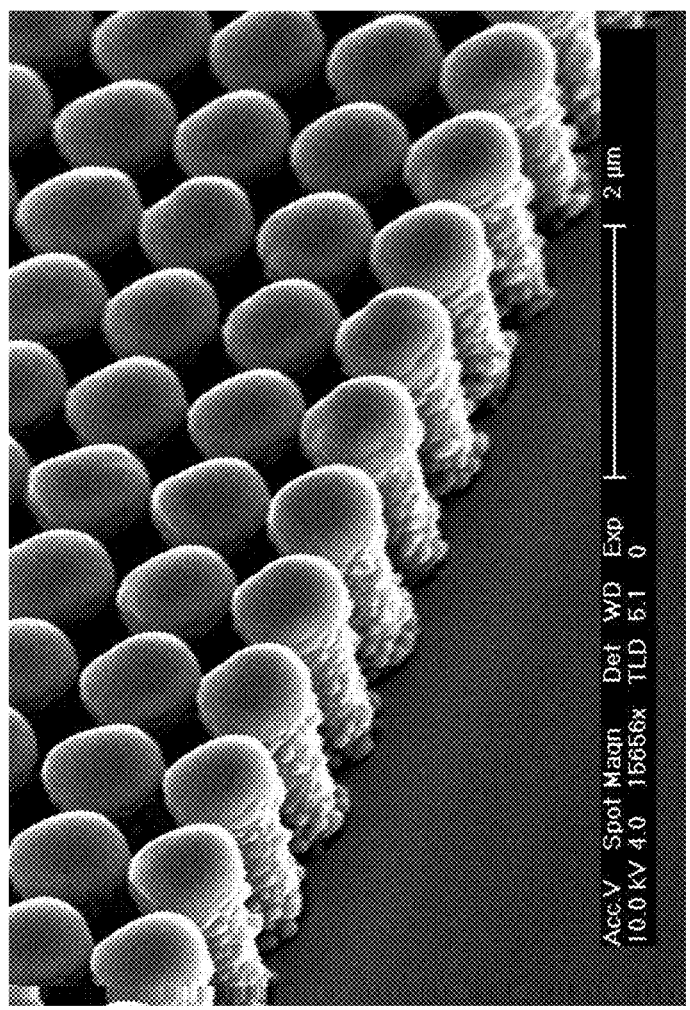

In order to test metal deposition ion beam induced deposition of Platinum for embodiments of the present disclosure, the following set up was used. First, deposition was performed using an FEI Nova 600 Nanolab ion beam source. 100 nm thick depositions was aligned directly over the pillar array electrodes. EDS analysis in an FEI Sition 200 SEM/EDAX machine was used to confirm the composition of the deposited layer. A resulting embodiment according to the present disclosure using the above procedure can be seen in FIGS. 18A and 18B.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. A method for fabricating three dimensional high surface electrodes, comprising:

designing a plurality of pillars by optimizing one or more characteristics of the pillars, wherein the plurality of pillars corresponds to one or more electrodes dependent on an isolation provided to the plurality of pillars;

applying a resist onto a substrate, wherein the substrate is silicon or silicon alloy;

patterning the resist, wherein the patterning defines the plurality of pillars to be formed on the substrate;

removing selected portions of the substrate via etching corresponding to the pattern of the resist to form the plurality of pillars, the etching forming a pillar with an aspect ratio greater than 5;

insulating a first group of pillars of the plurality of pillars from other pillars of the plurality of pillars to form one distinct electrode by forming an insulator layer with complete and uniform coverage over the first group of pillars of the plurality of pillars; and depositing a 10 nm to 500 nm metal layer on the plurality of pillars to increase the conductivity of a surface of the electrode, wherein the metal layer coverage is complete and uniform over the plurality of pillars.

2. The method according to claim 1, wherein the thickness of the insulator layer is between 50 nm and 250 nm.

3. A method for fabricating three dimensional high surface electrodes from CMOS on a metal that is not silicon, comprising:

designing a plurality of pillars by optimizing one or more characteristics of the pillars, wherein the plurality of pillars corresponds to one or more electrodes dependent on an isolation provided to the plurality of pillars;

selecting a top most metal layer from the CMOS where the pillars will be formed, wherein the top most metal layer is not silicon;

applying a resist onto the top most metal layer of the CMOS;

patterning the resist, wherein the patterning defines where the plurality of pillars will be formed on the top most metal layer of the CMOS;

removing selected portions of the top most metal layer of the CMOS via etching corresponding to the pattern of the resist to form the plurality of pillars, the etching forming a pillar with an aspect ratio greater than 5; and depositing a 10 nm to 500 nm metal layer on the plurality of pillars to increase conductivity of a surface of the electrode, wherein a coverage of the metal layer coverage is complete and uniform over the plurality of pillars, wherein the method for fabricating is performed at temperatures below 500° C.

4. The method according to claim 1, wherein the thickness of the metal layer is between 50 nm and 250 nm.

5. The method according to claim 1, wherein the pillars have an aspect ratio between 15 and 20.

6. The method for fabricating three dimensional high surface electrodes according to claim 1, further comprising:

depositing a plurality of particles on top of the metal layer of the plurality of pillars to increase the surface area of the pillars, wherein
the particles are deposited via spray or spin techniques, and
the particles are selected corresponding to a size of a species to be detected by the electrode.

7. The method according to claim 6, wherein the particles are either nanoparticles or microparticles.

8. The method according to claim 1, wherein the depositing of the metal layer on the plurality of pillars is performed using pressure and a stage adapted to be rotated and tilted with respect to the metal being deposited.

9. The method according to claim 8, wherein the pressure used during metal deposition is 20 mTorr.

10. The method according to claim 1, wherein the temperature is below 250° C.

11. The method according to claim 3, wherein the thickness of the metal layer is between 50 nm and 250 nm.

12. The method according to claim 3, wherein the pillars have an aspect ratio between 15 and 20.

13. The method for fabricating three dimensional high surface electrodes according to claim 3, further comprising:

depositing a plurality of particles on top of the metal layer of the plurality of pillars to increase the surface area of the pillars, wherein
the particles are deposited via spray or spin techniques, and
the particles are selected corresponding to a size of a species to be detected by the electrode.

14. The method according to claim 3, wherein the depositing of the metal layer on the plurality of pillars is performed using pressure and a stage adapted to be rotated and tilted with respect to the metal being deposited.

15. The method according to claim 3, wherein the temperature is below 250° C.

* * * * *